(12) United States Patent
Balle-Petersen et al.

(10) Patent No.: US 6,676,654 B1
(45) Date of Patent: Jan. 13, 2004

(54) APPARATUS FOR TISSUE TREATMENT AND HAVING A MONITOR FOR DISPLAY OF TISSUE FEATURES

(75) Inventors: Olav Balle-Petersen, Humlebaek (DK); Bjarne Asah, Taastrup (DK); Casper Dolleris, Vancouver (DK)

(73) Assignee: Asah Medico A/S, Hvidovre (DK)

( * ) Notice: Subject to any disclaimer, the term of this patent is extended or adjusted under 35 U.S.C. 154(b) by 75 days.

(21) Appl. No.: 09/662,373

(22) Filed: Sep. 13, 2000

Related U.S. Application Data

(63) Continuation-in-part of application No. PCT/DK00/00097, filed on Mar. 8, 2000, and a continuation-in-part of application No. 09/459,540, filed on Dec. 13, 1999, and a continuation-in-part of application No. 09/265,408, filed on Mar. 10, 1999, and a continuation-in-part of application No. PCT/DK98/00372, filed on Aug. 28, 1998, which is a continuation-in-part of application No. 08/974,429, filed on Nov. 19, 1997, now Pat. No. 6,074,382.

(30) Foreign Application Priority Data

Aug. 29, 1997 (DK) .................................... 0989/97
Mar. 8, 1999 (DK) ........................................ 1999 00325

(51) Int. Cl.$^7$ ............................................. A61B 18/18
(52) U.S. Cl. ............................... 606/9; 606/11; 606/17; 606/18
(58) Field of Search ..................... 606/9–11, 17–18; 600/108

(56) References Cited

U.S. PATENT DOCUMENTS

| | | |
|---|---|---|
| 3,307,553 A | 3/1967 | Liebner |
| 3,821,510 A | 6/1974 | Muncheryan |
| 4,140,130 A | 2/1979 | Storm, III |
| 4,587,396 A | 5/1986 | Rubin |
| 4,854,320 A | 8/1989 | Dew et al. |
| 4,913,132 A | 4/1990 | Gabriel |
| 4,938,205 A * | 7/1990 | Nudelman .................. 600/108 |
| 5,048,904 A | 9/1991 | Montagu |
| 5,057,104 A | 10/1991 | Chess |
| 5,106,387 A | 4/1992 | Kittrell et al. |
| 5,107,516 A | 4/1992 | Dressel et al. |
| 5,282,797 A | 2/1994 | Chess |
| 5,330,519 A | 7/1994 | Mason et al. |
| 5,344,418 A | 9/1994 | Ghaffari |
| 5,382,770 A | 1/1995 | Black et al. |
| 5,405,368 A | 4/1995 | Eckhouse |
| 5,456,260 A | 10/1995 | Kollias et al. |
| 5,474,549 A | 12/1995 | Ortiz et al. |
| 5,486,172 A | 1/1996 | Chess |
| 5,531,740 A | 7/1996 | Black |
| 5,588,428 A | 12/1996 | Smith et al. |
| 5,595,568 A | 1/1997 | Anderson et al. |
| 5,620,478 A | 4/1997 | Eckhouse |
| 5,628,744 A | 5/1997 | Coleman et al. |
| 5,630,811 A | 5/1997 | Miller |
| 5,653,706 A | 8/1997 | Zavislan et al. |

(List continued on next page.)

FOREIGN PATENT DOCUMENTS

| | | |
|---|---|---|
| DE | 3837248 A1 | 5/1990 |
| DE | 19852948 A1 | 5/2000 |
| EP | 0699038 B1 | 5/1994 |
| EP | 0763371 A2 | 3/1997 |
| EP | 0783904 A2 | 7/1997 |

(List continued on next page.)

Primary Examiner—Roy D. Gibson
(74) Attorney, Agent, or Firm—Birch, Stewart, Kolasch & Birch, LLP

(57) ABSTRACT

A method and apparatus for tissue treatment. A handpiece contains a light source for emitting a light beam toward the tissue. A detector detects at least one tissue parameter along a path during an initial scan. This information is stored and a map of the parameter produced. A light beam controller controls a light beam parameter and controls a deflector in order to apply the light beam to the tissue in a predetermined path.

57 Claims, 13 Drawing Sheets

U.S. PATENT DOCUMENTS

| | | |
|---|---|---|
| 5,720,772 A | 2/1998 | Eckhouse |
| 5,735,276 A | 4/1998 | Lemelson |
| 5,742,392 A | 4/1998 | Anderson et al. |
| 5,743,902 A | 4/1998 | Trost |
| 5,779,702 A | 7/1998 | Fard |
| 5,810,801 A | 9/1998 | Anderson et al. |
| 5,814,040 A | 9/1998 | Nelson et al. |
| 5,814,041 A | 9/1998 | Anderson et al. |
| 5,820,626 A | 10/1998 | Baumgardner |
| 5,830,208 A | 11/1998 | Muller |
| 5,833,612 A | 11/1998 | Eckhouse et al. |
| 5,836,939 A | 11/1998 | Negus et al. |
| 5,851,181 A | 12/1998 | Talmor |
| 5,853,407 A | 12/1998 | Miller |
| 5,860,968 A | 1/1999 | Wojcik et al. |
| 5,865,828 A | 2/1999 | Jeng |
| 5,868,731 A | 2/1999 | Budnik et al. |
| 5,868,732 A | 2/1999 | Waldman et al. |
| 5,957,915 A | 9/1999 | Trost |
| 5,995,867 A * | 11/1999 | Zavislan et al. ......... 250/461.2 |
| 6,074,382 A | 6/2000 | Asah et al. |
| 6,096,029 A | 8/2000 | O'Donnell, Jr. |
| 6,110,195 A | 8/2000 | Xie et al. |
| 6,162,211 A * | 12/2000 | Tankovich et al. ............. 606/9 |

FOREIGN PATENT DOCUMENTS

| | | |
|---|---|---|
| EP | 0788765 A1 | 8/1997 |
| EP | 0827716 A2 | 3/1998 |
| EP | 0880941 A1 | 12/1998 |
| EP | 0 898 983 A1 | 3/1999 |
| EP | 0933096 A2 | 8/1999 |
| WO | WO 8606527 | 11/1986 |
| WO | WO 9308877 | 5/1993 |
| WO | WO 93/16631 | 9/1993 |
| WO | WO 9400194 | 1/1994 |
| WO | WO 9503089 | 2/1995 |
| WO | WO 9625979 | 8/1996 |
| WO | WO 9824514 | 6/1998 |
| WO | WO 9825528 | 6/1998 |
| WO | WO 9833558 | 8/1998 |
| WO | WO 9846133 | 10/1998 |
| WO | WO 98/49963 | 11/1998 |
| WO | WO 9851235 | 11/1998 |
| WO | WO 9855180 | 12/1998 |
| WO | WO 9857588 | 12/1998 |
| WO | WO 9917668 | 4/1999 |
| WO | WO 9946005 | 9/1999 |

* cited by examiner

APPARATUS FOR TISSUE TREATMENT AND HAVING A MONITOR FOR DISPLAY OF TISSUE FEATURES

This application is a CIP of Ser. No. 09/459,540 filed Dec. 13, 1999 which is a CIP of Ser. No. 08/974,429 filed Nov. 19, 1997 U.S. Pat. No. 6,074,382 and a CIP of PCT/DK98/00372 filed Aug. 28, 1998 and said Ser. No. 08/974,429 filed Nov. 19, 1997 is a CIP of PCT/DK00/00097 filed Mar. 8, 2000.

FIELD OF THE INVENTION

The present invention relates to an apparatus for tissue treatment, such as cosmetic tissue treatment.

BACKGROUND OF THE INVENTION

It is known to utilise laser light for tissue treatment, such as cosmetic tissue treatment, such as dermal ablation, removal of hair, photocoagulation of veins, etc.

During dermal ablation, a laser ablates a thin epidermal layer of illuminated derma of a patient. During healing, a new epidermal layer is formed on the ablated surface having the look of the derma of a young person; i.e. the new epidermal layer is formed without previously existing scars, wrinkles, etc.

Lasers that operate at a wavelength that is absorbed in water are used for dermal ablation. When the laser power density (W/mm$^2$) at illuminated cells is sufficient, cellular water is superheated causing small explosions that disrupt heated cells.

During photocoagulation of veins, such as spider veins or spider nevi, regions along the vein are subject to selective photothermolys is. The vein is cut off and the pigment, usually blood, is eventually reabsorbed by the body of the patient.

Hair removal is effected by directing a laser beam at a hair follicle to destroy the hair follicle and its adjacent blood vessels by the heat produced by photothermolysis.

During treatment of tissue, such as an epidermal layer, hair, veins, etc, it is essential not to damage underlying or surrounding tissue. Residual heat may cause untreated cells to char and become necrotic, whereby scars may be formed. Thus, it is desirable to apply laser power only to tissue to be treated and only for a short time, to minimise transmission of conducted heat to underlying and surrounding tissue.

To some extend this has been obtained by selective photothermolysis, i.e. laser light is utilised having a wavelength that is selectively absorbed by tissue to be treated and that is not absorbed by the surrounding and healthy tissue. The selective absorption of the laser light causes selective photothermolysis in the tissue to be treated.

It is also known to automatically control whether or not light is transmitted towards tissue of a certain type. In U.S. Pat. No. 5,531,740, an apparatus is disclosed for automatically delivering a laser beam to an intricated coloured region of a treatment area, e.g. for laser photocoagulation treatment of malformed veins. Typically, venular malformation forms an extremely intricate pattern and consequently, the task of precisely delivering the laser beam exclusively to the malformed veins becomes quite formidable. During scanning over the treatment region, the colour of tissue to be treated is detected and the laser automatically treats only areas having a specified colour.

It is a disadvantage of the apparatus that it is bulky and cannot easily be moved into treatment positions in relation to various surfaces of a human body. Rather, a tissue surface to be treated has to be brought into a specific position in relation to the apparatus before treatment can take place.

It is still another disadvantage of the known apparatuses that the distance between the surface to be treated and the output laser beam optics is unknown so that the degree of focusing of the laser beam on the surface to be treated is dependent on the operator.

It is yet another disadvantage of known apparatuses that no feedback on the quality of the treatment currently in progress is provided.

SUMMARY OF THE INVENTION

It is therefore desired to accurately control the amount of light energy transferred to tissue to be treated. The amount of energy must be sufficient for the treated cells to photothermolyse, i.e. decompose because of heat generated by light absorption, and, simultaneously, the amount of residual energy heating untreated cells must be so low that untreated cells will not be damaged.

It is an object of the present invention to provide an apparatus for tissue treatment in which one or more tissue parameters are detected and comprising a display for displaying tissue features based on the detected tissue parameters.

It is another object of the present invention to provide an apparatus for tissue treatment, comprising user interface means for selecting areas of tissue for treatment based on the displayed tissue features.

It is yet another object of the present invention to provide an apparatus for tissue treatment in which parameters of the laser beam is automatically adjusted according to one or more detected tissue parameters. This may facilitate different treatment of different tissue features in a single operation.

It is a further object of the present invention to provide an apparatus for tissue treatment that include means for detecting the distance between the surface of tissue to be treated and the output optics focusing treating light onto the tissue so that optimum focusing conditions may automatically be obtained during treatment.

It is still another object of the present invention to provide an apparatus for tissue treatment that includes a temperature measuring device for measurement of tissue temperature.

It is yet still another object of the present invention to provide an apparatus for tissue treatment that is adapted to automatically and accurately treat tissue to a desired depth causing only a minimum of damage to surrounding tissue that are not treated.

According to the present invention, the above-mentioned and other objects are fulfilled by an apparatus for tissue treatment, comprising a light source for emission of a light beam towards tissue to be treated, a handpiece with an output for emission of the treating light beam, a detector means for detection of at least one tissue parameter, and a display for displaying a map of the at least one tissue parameter.

According to another aspect of the present invention, the above-mentioned and other abjects are fulfilled by an apparatus for tissue treatment having a light source for emission of a treating light beam towards tissue to be treated, detector means for detection of tissue temperature and a display f or displaying a map of tissue temperature.

The light beam ma y be emitted from a handpiece.

The handpiece may be adapted to be held in one hand by an operator and may be freely manipulated for easy aiming of the light beam towards various areas of a patient.

It is preferred to shape the handpiece ergonomically so that a comfortable hand grip is provided for the operator of the apparatus. For example, it is preferred to direct the light beam towards a target area at a substantially right angle to the area. The ergonomic form of the handpiece allows the operator to point the light beam at a substantially right angle to the target surface without having to bend the wrist in an uncomfortable way.

Preferably, the handpiece is light so that it is easy for the operator to hold the handpiece and bring it into any desired position in relation to the target surface to be treated. The weight of a preferred handpiece according to the present invention—interconnecting cables not included—is less than 500 grams, such as 290 grams, or such as 250 grams.

The handpiece may comprise the light source, such as a laser, such as a solid state laser, e.g. a laser diode.

Alternatively, the apparatus may comprise an optical fibre for transmission of the light beam from the light source to the handpiece. The fibre has a beam-inlet end that is aligned with the emitted light beam so that a light beam is coupled into the optical fibre and a beam-outlet end for emission of the transmitted light beam. The handpiece is coupled to the optical fibre at the beam-outlet end and comprises an output for emission of the light beam towards a target area of tissue to be treated.

It is preferred, that the light source utilised in the present invention is a laser, but other light sources, such as light emitting diodes and halogen bulbs, may be utilised.

The power emitted by the light source utilised is dependent on the specific application of the light source. For example, when removing hairs, a method is disclosed in U.S. Pat. No. 5,925,035, ThermoLase Corporation, wherein a substance, such as a mixture of carbon particles and oil, may be applied to the tissue area to be treated. The substance may then enter the hair duct and light of a wavelength readily absorbed in the substance may illuminate the area to be treated. The power of the light source, preferably a laser, such as a Nd YAG laser, is then chosen so that the carbon particles are heated to a temperature sufficient to devitalise the tissue feeding the hair so that the hair dies.

Another example is the use of the light source to merely activate cells, such as tissue cells, bacteria, or viruses being present in or at the tissue. These cells may be present inherently or they may be applied e.g. for the purpose of Photon Dynamic Therapy, and in most cases the cells to be treated are undesired and the aim of the treatment is to destroy, activate, damage or in any other way affect the cells to obtain a desired treatment of these cells.

Alternatively, the light source may be any laser capable of emitting light with sufficient power for illuminated cells to decompose, such as $CO_2$ lasers, YAG lasers, such as Erbium YAG lasers, Holmium YAG lasers, Nd YAG lasers, etc., semiconductor lasers, pulsed lasers, gas lasers, solid state lasers, Hg lasers, excimer lasers, etc.

Thus, the laser may be used for ablating a thin epidermal layer of the derma of a patient, removing marks on the tissue, such as marks from chloasma, liver spots, red spots, tattoos, blood vessels just below the surface, etc, as well as warts, wounds, hair follicles, etc.

Present $CO_2$ lasers emit light at a wavelength of 10600 nm. The $CO_2$ laser is particularly well suited as a light source in an apparatus for ablating dermal cells as water has a high energy absorbance at 10600 nm and the $CO_2$ laser is capable of reliably delivering the required laser power.

Erbium YAG lasers emit light at a wavelength of 2930 nm. Water absorbs less energy at this wavelength than at 10600 nm. Therefore, the Erbium YAG laser may be preferred for ablating thinner layers of dermal cells than may be ablated with a $CO_2$ laser. Tissue having been treated with light emitted from an Erbium YAG laser may heal faster than tissue having been treated with $CO_2$ laser light as a thinner layer of dermal cells is influenced by Erbium YAG laser light. An Erbium YAG laser may also be preferred when photocoagulation of blood vessels should be avoided.

A CO laser emits light in the 4500 nm to 5500 nm wavelength range. Water absorption at these wavelengths is somewhat less than water absorption at 10600 nm. A CO laser light source is presently preferred for dental treatment, e.g. for removal of carries, as dentine is not influenced by illumination of light from a CO laser.

A Nd YAG laser with a frequency doubled output beam in the 520–680 nm wavelength range is presently preferred as a light source for treatment of hypervasculation. Light in this wavelength range causes photocoagulation of blood without affecting surrounding tissue provided that an appropriate intensity of the light beam is directed towards the microvessels for an appropriate period of time. Coagulation stops blood flow in the treated vessels whereby discoloration of the skin also stops.

Cellular water absorbs light energy, and applying light energy to the cells is therefore an efficient way of ablating tissue. Thus, for tissue ablation, it is preferred to use light sources, such as lasers, generating light at wavelengths with a high absorption in water, preferably wavelengths larger than 190 nm, such as wavelengths in the range from 190 nm to 1900 nm, preferably from 700 nm to 900 nm, and even more preferred approximately 810 nm, or, preferably wavelengths larger than 1900 nm, such as wavelengths in the range from 1900 nm to 3000 nm, preferably from 1900 nm to 2200 nm, preferably from 1900 nm to 2100 nm, or, from 2800 nm to 3000 nm, and even more preferred approximately 2930 nm, or wavelengths equal to or greater than 4500 nm, such as wavelengths in the range from 4500 nm to 11000 nm, preferably from 4500 nm to 5500 nm, alternatively from 10000 nm to 11000 nm, such as around 10600 nm.

Typically, a power density greater than about 50 $W/mm^2$, such as a power density in the range from about 50 $W/mm^2$ to about 180 $W/mm^2$, is adequate for vaporising cells with a minimum of damage to the surrounding tissue.

However, when removing hairs, the wavelength of the light is preferred to be approx. 810 nm. At this wavelength the absorption of the light in the hair follicles is lower than at higher wavelengths, and the energy density must therefore be higher than 50 $J/cm^2$, preferable not higher than 150 $J/cm^2$, preferably approximately 100 $J/cm^2$. The pulse width may vary from 50 ms and to several seconds. In one preferred embodiment of the invention a pulse width of 50–100 ms, such as approx. 100 ms, is used. But also longer pulse widths, such as pulse widths of 50 ms–3 seconds, such as 50–500 ms, or such as 100 ms–1 second, such as approx. 250 ms, approx. 500 ms, or such as approx. 1 second, may be used.

Generally, the power density and/or the energy density is adapted to the wavelength applied and the tissue to be treated.

The optical fibre for interconnection of the light source with the handpiece according to an embodiment of the present invention may be any fibre, such as a polycrystalline silver halide fibre for transmission of infrared light, etc, that is suitable for transmission of light emitted from the light source and that is made of a material that allows repeated bending of the fibre, so that the handpiece can be freely manipulated for easy aiming of the light beam towards various areas of a patient. It is of course envisaged that the fibre used is adapted to the applied light source. For the interconnection of a light source emitting light in the visible wavelength range or near infrared range it is preferred to use a quartz fibre doped according to the specific wavelength range.

Tissue or tissue features may be classified into specific tissue types according to predetermined values of various parameters, such as colour, temperature, texture, elasticity, size, shape, etc.

For example, various tissue features, such as marks on the tissue, such as marks from chloasma, liver spots, red spots, tattoos, blood vessels just below the surface, etc, as well as warts, wounds, hair follicles, etc, may be detected by their colour. Thus, the detector means may comprise light detectors for detection of intensity of light emitted from tissue at the target area, the target area being the area to be treated by the light beam or being the area the handpiece is currently directed at.

Further, certain types of tissue, such as small marks on the tissue such as marks from chloasma, liver spots, red spots, tattoos, blood vessels, beauty spots, freckles, etc, to be treated are characterised by the shape or the size of the area covered by the type of tissue in question. For example, when treating different types of marks of substantially identical colours it may be desirable to treat each type of mark differently and according to the respective size or shape of the type of mark in question.

The light detector is preferably a semiconductor light detector, such as a photodiode, etc.

The light detector may be positioned inside the handpiece.

The target area may be illuminated by an illuminating light source, such as a white light source, and the reflected light from the target area may be detected by the detector means and analysed so as to characterise the type of tissue that is illuminated.

Further, illuminating light sources emitting light of different predetermined wavelengths towards the target area may be provided. For example, the illuminating light sources may comprise two light emitting diodes, one for emission of light in the wavelength range where the light is considered red and the other for emission of light in the wavelength range where the light is considered green. Also the illuminating light sources may comprise three, four or even more light emitting diodes for emission of light of different wavelength ranges. The light sources may alternatively emit light in the ultra violet or infrared wavelength range. Light from the light sources is transmitted towards the target area and is reflected by tissue at the target area. The reflected light is detected by the detector means and the intensity of reflected light in the two or more wavelength ranges in question characterises one or more parameters of tissue that is illuminated.

The illuminating light source or light sources illuminating the target area may be positioned inside the handpiece.

The apparatus for tissue treatment may comprise an infrared detector, such as an infrared photo detector, for detection of intensity of infrared light emitted from tissue at the target surface, e.g. for determination of the temperature of the tissue. Like colour, temperature may be utilised for characterisation of tissue features. Further, tissue temperature may be utilised for monitoring of treatment progress and quality. The temperature of treated tissue increases during treatment and measurement of tissue temperature may be utilised for verification of the effect of the treatment. For example, when a specific tissue temperature is reached within a specific area, treatment of that tissue may be terminated, e.g. further treatment may be inhibited, as sufficient treatment has already been accomplished. Further, if a certain temperature has not been reached during treatment, output power of the light source may be increased to increase efficiency of the treatment.

The infrared detector may be positioned in the handpiece.

The apparatus is adapted to display a map of tissue features of an area of tissue on a display unit, such as a CRT, an LCD, a TFT display, etc. Tissue features may be characterised by specific values of certain parameters, such as colour, temperature, thickness, texture, elasticity, size, and shape, etc, or by values of mathematical functions of such parameters.

Tissue features may be displayed as graphical three dimensional plots showing surface profiles of selected mathematical functions of tissue parameters of the mapped area.

Alternatively, tissue features may be displayed as a colour map, i.e. predetermined ranges of values of a selected mathematical function of tissue parameters are allocated selected colours to be displayed in areas of the map mapping tissue areas with the respective function values.

Further, the functions may include averages, weighted averages, correlations, cross-correlations, etc, of mathematical functions.

The display unit may be positioned on the handpiece.

The apparatus may further comprise user interface means for selection of specific tissue areas for treatment based on the displayed tissue map. For example, the display unit may comprise a touch screen for displaying the tissue map and an operator of the apparatus may select a tissue area for treatment by touching the corresponding area on the touch screen.

Alternatively, the user interface means may conventionally comprise moving a pointer on the display unit for pinpointing tissue areas to be treated, such as means for moving, such as a mouse, a track ball or a roller key, such as a roller corresponding to the smart Navi Roller from Nokia.

For example, beauty spots may be distinguished from surrounding tissue by their colour. Thus, the displayed map may show the tissue area in natural colours, e.g. as recorded by a video camera, such as a CCD camera. The operator of the apparatus may then, in any conventional manner, select the beauty spots to be removed, such as by moving a pointer on the display unit around a beauty spot thereby selecting the surrounded area for treatment, or, the apparatus may comprise image processing software detecting and marking areas with a beauty spot that will be treated if selected by the operator, e.g. by touching the marked area to be treated.

Likewise, the displayed map may show the temperature of a mapped tissue area, e.g. by displaying specific temperature ranges in specific colours. The temperature map may be used to verify the result of a treatment of the tissue. Areas with temperatures within certain temperature ranges may be selected by the operator as previously described for further treatment.

Further, several maps may be displayed simultaneously on the display unit, e.g. utilising overlay techniques. For example, a map of tissue showing the tissue in natural colours may be overlaid by a temperature map whereby temperatures of certain tissue features, e.g. temperatures of beauty spots after treatment, are indicated to the operator.

The handpiece may comprise deflection means for adjustable deflection of the light beam emitted towards tissue to be treated.

When the handpiece is kept in a fixed position in relation to a target surface which is illuminated by the light beam, changing of the position of the deflection means causes the light beam to traverse or scan the target surface along a path or a curve. An area may be traversed or scanned by the light beam, e.g. by letting the light beam traverse or scan a meander like path substantially covering the area or, by traversing or scanning the area line by line. In the present context, the type, number and shape of paths traversed by the light beam in order to traverse a specific area is denoted the traversing pattern or the scan pattern. The area that is scanned or traversed by the light beam is denoted the scan area, the treatment area or the traversed area. The light beam may treat the surface at the target area and the light beam is therefore also denoted the treating light beam.

The deflection means may comprise any optical component or components suitable for deflecting light of the wavelength in question, such as mirrors, prisms, diffractive optical elements, such as holograms, grids, gratings, etc, etc.

Further, the handpiece may comprise the deflection means.

The deflection means are preferably adjustably mounted for displacement of the deflection means as a function of time, so that the light beam may traverse a surface along a predetermined path, while the apparatus is kept in a fixed position. Preferably, the deflection means are rotatably mounted, and the actual deflection of the light beam is determined by the current angular position of the deflection means. This is a particular advantage when the handpiece comprises the deflection means as the handpiece then may be kept in a fixed position during scanning of the surface target area whereby scanning of the surface is not depending on operator skills. Moving means may be utilised to control positions of the deflection and focusing means, such as actuators, such as piezo electric crystals, the displacement of which is controlled by applying a specific electric voltage to their electrodes, electromotors generating linear or rotational displacements, galvanometers, magnetically activated or controlled actuators, pneumatic actuators, hydraulic actuators, etc.

The positions of the deflection means may be controlled by deflection control means adapted to control the deflection means to deflect the light beam in such a way that it traverses a target surface along a predetermined path.

According to an embodiment of the invention, an apparatus is provided, having two mirrors that are rotatably mounted in the path of the light beam in the apparatus. The rotational axis of the mirrors may be substantially perpendicular to each other in order to obtain two dimensional deflection of the light beam. Further, a handpiece may be provided having the two mirrors rotatably mounted in the path of the light beam in the handpiece.

Alternatively, the deflection means may comprise one mirror that is rotatable around two axes that may be substantially perpendicular to each other.

The mirrors may be connected to electromotors for angular positioning of the mirrors, e.g. each mirror may be directly connected to a corresponding shaft of a motor, whereby each motor is used for angular positioning of the corresponding mirror.

In order to minimise the size of the handpiece, it is preferred to mount the motors with their respective shafts in a common plane. For example, one motor may be a linear motor, such as a linear step motor, generating linear displacements. The shaft of this motor may be connected to the mirror at a first edge of the mirror, while a second and opposite edge of the mirror is rotatably connected to the handpiece. By pushing or pulling the first edge by the linear motor, the mirror is rotated about its rotational axis. The other motor, preferably a galvanometer, may be connected to the other mirror in the conventional way described above, whereby the two mirrors may be rotated around substantially perpendicular axes.

The deflection control means may be adapted to control the deflection means so that the predetermined path is a substantially straight line.

Preferably, the deflection control means are adapted to control the deflection means so that the light beam traverses a target surface area line by line.

It is an important advantage of the line by line scan pattern that areas of any arbitrary shape, such as polygonal, such as rectangular, quadratic, triangular, etc, or circular, elliptic, etc, may be traversed line by line by appropriately controlling the starting point and stopping point of light emission along each line traversed.

Preferably, the first deflection control means are adapted to control the first deflection means so that the lines are traversed sequentially i.e. neighbouring lines are traversed successively without interleaving. Thus, neighbouring lines are traversed within a very short time period so that time will be insufficient for involuntary hand movements of the operator to move the handpiece back to the line previously scanned which would lead to uneven treatment of the target surface. Thus, the requirement for the operator to be able to keep the handpiece steady in a desired position is hereby minimised.

In interlaced scanning every second line of the target surface area is scanned successively and after that the remaining lines in-between are successively scanned. Thus, there would be sufficient time between scanning of neighbouring lines to allow involuntary movements of the operator to move the handpiece back to a line previously scanned. Hereby, some areas may be subjected to repeated treatment whereby tissue may be damaged while other areas may be left without treatment.

Preferably, the first deflection control means is adapted to control the first deflection means so that the lines are scanned in the same direction. Thereby, substantially the same amount of power per area is delivered uniformly across the target surface area leading to substantially the same temperature increase at any point of the target surface area after scanning.

When a target area is traversed line by line, it is preferred that movement of one mirror causes the light beam to traverse a line while movement of the other mirror moves the light beam to the next line. In the example above, the galvanometer preferably generates the line scanning as the galvanometer can move the mirror at a high speed, and the linear motor preferably generates the displacement of the light beam to the next line to be traversed.

As mentioned earlier, when cells are to be ablated it is preferred to control the amount of energy delivered to the cells to be ablated, as the amount of energy must be sufficient for the dermal cells to vaporise and, simultaneously, the amount of residual energy heating non-ablated cells must be so low that non-ablated cells will not be seriously damaged. Thus, when an area of tissue is traversed, e.g. line by line, it is preferred that neighbouring lines substantially abut each other. Clinical investigations have shown that, typically, an overlap of 0.1 to 0.2 mm is acceptable, and a distance between traversed lines of up to 0.1–0.2 mm is acceptable.

In order to control positioning of paths on the target area this accurately, it is preferred to position the deflection means extremely accurately e.g. in the handpiece. In the preferred embodiment of the invention, this is accomplished by utilisation of printed circuit technology providing high accuracy of hole positioning of 0.05 mm. The mirrors are rotated around shafts that are mounted in printed circuit boards providing the required positioning accuracy. Further, the motors rotating the mirrors are also mounted on the printed circuit boards providing electrical connections to the motors and the mechanical support and positioning needed.

When scanning a target surface area line by line, it is for applications, such as ablation of tissue or destruction of bacteria or viruses, preferred to traverse each line in the same direction ensuring uniform heating of cells across the target surface area. Further, it is preferred to turn off the light beam, e.g. by switching off the light source, by inserting a light obstructing member in the light path of the beam, etc, while the light beam is moved from the end of a line having been traversed to the start of the next line to be traversed, in order to avoid repeated illumination of areas of the two lines. It is thus preferred that the lines are abutting each other and not overlapping.

Instead of turning the light source off, the light beam may be moved at a speed significantly larger than the scanning speed, during movement from the end of a line to the start of the next line.

In other applications, for example when the objective of the treatment is removal of hairs, it is preferred to scan the target surface area by a light beam illuminating a spot size at the target area being larger than the spot size usually applied by ablation of tissue, the spot size applied ranging from 1 to 9 mm, preferably from 2 to 8 mm, more preferred from 2 to 6 mm, or most preferred the spot size is approximately 3 mm. When removing hairs, it is preferred to scan the tissue along a curve in steps whereby the illuminated spot is allowed to stay in a specific treating position 60–100 ms, preferably approximately 80 ms, followed by movement of the spot to the next treating position within a few milliseconds. Preferably, the distance between two succeeding treating spot positions is less than a spot diameter, such as approximately half a spot diameter, such as between half a spot diameter and a diameter of the spot, so as to provide for a controlled overlap of the spots resulting in an effective hair removal. The thus implied overlap ensures a uniform distribution of energy across the traversed tissue area, and thus a uniform removal of hairs. It is further preferred to scan the tissue area along a meander curve constituted by lines scanned successively in opposite directions having a spot overlap such as mentioned above.

Typically, the intensity within the beam of a light beam as generated by the light source varies as a normal function of the distance from the centre of the beam. The optical fibre may be designed or selected to be dispersive in such a way that the intensity function of the light beam emitted from the fibre as a function of the distance to the centre of the beam is substantially rectangular, i.e. the intensity of the beam leaving the fibre decays more slowly towards the edge of the beam than the intensity of a beam as generated by the light source whereby heat is more uniformly generated in cells across a traversed line of tissue.

However, when using large spot sizes, such as the spot sizes used when removing hair, the intensity function of the light beam emitted from the fibre is not substantially rectangular, whereby a spot overlap as mentioned above is necessary to obtain a uniform distribution of heat.

The apparatus may further comprise light beam control means comprising outputs for controlling various parameters of the light beam emitted by the light source, such as wavelength, output power, duty cycle, active time, pulse width, inter pulse delay, etc. Based on mathematical functions of tissue parameters as measured by the detector means, the light beam control means adjusts corresponding parameters of the emitted light beam. For example, when two illuminating light sources are utilised for detection of tissue parameters as previously described, predetermined reflected light intensity value ranges for the two wavelength ranges may be stored in a memory of the light beam control means. During treatment, measured values of reflected light intensity are compared with the stored predetermined ranges and when measured values are within the stored ranges treatment is enabled and otherwise it is disabled.

Treatment may be disabled by stopping the emission of the light beam by shutting off the light source or by inserting a shutter in the path of the light beam. Alternatively, the parameters of the light source emitting the light beam may be controlled (e.g. by lowering the output power of the light source) so that tissue at the target area is not influenced by the light beam.

Further, the wavelength and/or the power of the light beam emitted by the light source may be adjusted according to the measured values. For example, a plurality of predetermined ranges of reflected light intensity may be stored in the memory and during treatment the measured values may be compared to the stored ranges and the value of the wavelength and/or the power of the light beam may be set according to relations between measured values and stored ranges. Alternatively, the light beam control means may calculate and control the wavelength and/or the power of the light beam as a predetermined function of measured values of reflected light.

The output power of the light beam may be adjusted by adjustment of the continuous output power of the light source, by adjustment of the duty cycle of the light source, etc.

The detector means may be utilised for detection of various tissue parameters during scanning of the light beam across a tissue area so that treatment and tissue parameter determination are performed substantially simultaneously including automatical adjustment of light beam parameters according to detected tissue parameter values.

Current values of light beam parameters may be displayed on the display unit together with the tissue map.

The user interface means may comprise means for modifying one or more of the automatically adjusted light beam parameters.

The apparatus may be adapted to continuously update the tissue map during treatment so that actual tissue parameters are displayed in real time whereby the operator can follow the effects of the treatment in real time, which will allow the operator to modify light beam parameters during treatment in response to the displayed results of the treatment.

The apparatus may further comprise tissue parameter storage means, such as an EEPROM, a flash EEPROM, a hard disk, etc., for storage of coherent data sets of signal values provided by the detector means at positions along the path traversed by the treating light beam during treatment and the corresponding positions themselves thereby mapping tissue parameters as a function of stored relative positions along the path. Further, the light beam control means may be adapted for controlling parameters of the light beam during a second movement of the light beam along the above-mentioned predetermined path in accordance with the coherent data sets stored.

For example, without automatic control of tissue treatment, removal of hair, removal of callosities, such as Millner spots or other small spots which are easily discriminated from the surrounding tissue, is a difficult task to perform as a large number of small spots having diameters of 100 Πm–3 mm, such as 200 Πm–2 mm, such as 500 Πm–1.5 mm, such as approximately 0.5 mm, such as approximately 1 mm, have to be pinpointed by the operator performing the treatment. According to the present invention, the apparatus scans the surface tissue area with hair to be removed without treatment. Hereby the hair follicles are detected by colour determinations as described above and their positions along the scanned path of the light beam are stored in the tissue parameter storage means and the corresponding tissue map is displayed on the display. The operator then selects specific areas of the map for treatment or selects treatment of the entire scanned area. Treatment light beam parameters may be displayed and the operator may choose to adjust the light beam parameters proposed by the apparatus. During a second scan of the tissue area and within the tissue areas selected for treatment, the light beam is turned on and off according to the content of the tissue parameter storage means and the selected light beam parameters so that solely the hair follicles detected during the first scan and positioned within areas selected for treatment are treated preventing the surrounding tissue from being damaged. Alternatively, the parameters of the light beam are automatically adjusted according to the content of the tissue parameter storage means so that when the light beam impedes on a hair follicle within an area selected for treatment, the power-per-area of the light beam is adjusted so that the detected hair follicles are destroyed and when the light beam impedes on tissue without a hair follicle the power-per-area of the light beam is reduced so that this surrounding tissue is not damaged. The user interface means comprising the display may be positioned on the housing of the handpiece.

The parameters may comprise scanning velocity of the treating light beam from the handpiece, intensity of the treating light beam emitted form the handpiece, size of the target surface area to be scanned by the treating light beam, shape of the target surface area to be scanned by the output light beam, etc.

The user interface means may comprise a first button, such as a membrane switch, a touch key on the display, etc, for selection of a parameter type by stepping through a set of parameter types, such as the set listed above or any subset thereof.

The user interface means may further comprise a second button for selection of a parameter value of the parameter type currently selected by stepping through a corresponding set of parameter values. Preferably, the parameter values are displayed on the display. Alternatively or concurrently, a set of light emitting diodes may be provided for indication of the set of currently selected parameter values.

It is an important advantage of provision of the user interface comprising the display at the handpiece that an operator of the handpiece is able to simultaneously select operational parameters of the handpiece and observe resulting changes in treatment effects since the operator is not forced to shift his field of view from the surface area to be treated to a user interface panel positioned somewhere else, e.g. behind the operator.

Preferably, the buttons are positioned on the housing of the handpiece so that single-handed operation is possible, preferably, with the right as well as with the left hand.

The user interface means may further comprise a foot pedal. The light beam traverses a target surface area when the operator depresses the pedal. Preferably, light beam scanning is stopped immediately when the operator releases the pedal and the emission of the light beam towards the target surface area is prevented.

Furthermore, a cooling fluid, such as water, such as a gel, etc. may be applied to the surface to be treated during treatment. For example, the fluid may be applied between two plates of a material transparent to the light beams to be used during treatment. The fluid may be positioned in a substantially closed reservoir between the two plates or the reservoir maybe provided with an in-let and an out-let whereby the fluid may pass through the reservoir to ensure constant cooling during treatment.

Thus, the apparatus may comprise a cooling member that is adapted to be positioned at the target area for cooling of tissue at the target area and that is at least partly transparent to the light beam. The cooling member may comprise a frame, an upper window positioned in the frame, and a lower window positioned in the frame, the frame, the upper window, and the lower window defining a volume therebetween for receiving and holding a cooling liquid. Further, the cooling member may comprise an inlet for inputting cooling liquid to the volume and an outlet for outputting cooling liquid from the volume. The cooling member may be attached to the handpiece.

To obtain an optimum result of treatment, it is important to keep the light beam focused at the target area during treatment.

The apparatus may comprise means for automatically controlling the distance from the apparatus to the focus point in such a way that the light beam is automatically focused at the target area during treatment. For example, if the handpiece comprises the means for automatically controlling, the distance from the handpiece to the focus point is controlled.

Thus, the detector means may comprise a detector array and array optics for forming an image of the target area on the array. Further, the detector means may comprise image processing means for processing output signals from the detector array.

Preferably, the image processing means is adapted to calculate the size of a spot on the target area illuminated by the light beam, or another light source of the apparatus, and imaged onto the detector array.

The apparatus may further comprise output optics for focusing the light beam onto the surface of tissue to be treated and movably positioned at the output of the apparatus for adjustment of the distance between the apparatus and the focus point, and focus control means for adjusting the position of the output optics in response to the value of the calculated spot size.

For example, the handpiece may comprise the output optics for focusing the light beam onto the surface of tissue to be treated whereby the distance between the handpiece and the focus point is adjusted by adjusting the position of the output optics in response to the value of the calculated spot size.

According to another embodiment of the invention, two crossing visible light beams are emitted from the handpiece, the cross point of the beams indicating the focus point of the treating beam. The image processing means are adapted to detect the number of spots imaged onto the detector array, and the focus control means are adapted to adjust the position of the output optics in response to the number of spots and, preferably, the distance between them (if more than one).

Alternatively, a number of light beams may be emitted from the handpiece, the light beams forming a cone of light, the diameter of the cone at the tissue surface indicating the focus point of the treating light beam.

In a preferred embodiment of the invention, the light beam control means further comprises switching means for preventing emission of the light beam and being controlled by the light beam control means so that emission of the light beam is prevented during a detecting scan from a predetermined first position to a predetermined second position along a predetermined path. During the detection scan the detector means detect light reflected from the target surface area along the predetermined path and the reflected light is analysed by the detector means or alternatively the reflected light is analysed by a microprocessor common to the control means of the apparatus.

By pulse width modulating the light source, energy delivered to the target surface may be varied along a traversed line in addition to the variations created by adjustment of parameters of the light beam in response to detected tissue parameters. A fade-in area may be created by starting scanning of each traversed line with short pulses of light between longer periods of no light. As the line is traversed, the duration of the light pulses may be increased while the periods with no light may be decreased. Outside the fade-in area, the light beam may not be pulsed whereby the remaining part of each line is traversed with a constant intensity of the light beam.

Likewise, a fade-out area may be created by after having traversed a part of a line with constant light intensity, pulse width modulating the light source to transmit shorter and shorter pulses of light towards the line at the target surface area ending with no light transmitted at the end of the line.

The maximum amount of energy delivered by the light beam to the target area is determined by the fade-in or fade-out function and can not be exceeded by the adjustment of parameters of the light beam. However, the adjustment may result in a amount of energy delivered that is lower than the maximum amount of energy.

The fade-in or fade-out scanning patterns may also be created by gradually increasing or decreasing, respectively, the power of the light source, or by decreasing or increasing, respectively, the scanning speed of the light beam.

Alternatively, a combination of these methods may be used.

The shape of the traversed area including the fading area may for example be polygonal, such as rectangular, quadratic, triangular, etc, circular, elliptic, etc.

A traversed line with fade-in and/or fade-out provides a smooth transition from a non-ablated area of tissue to an ablated area of tissue. This is a particularly advantageous feature when the apparatus according to the present invention is used for treatment of small marks on the tissue such as marks from chloasma, liver spots, red spots, tattoos, blood vessels etc.

Light intensity control means may be provided for generating a control signal for transmission to a light source interconnected with the optical fibre and controlling intensity of light emitted by the light source and transmitted through the optical fibre.

The fade-in and fade-out may be provided by controlling the intensity of the light beam and/or the velocity of the scanning light beam along a predetermined path and the light intensity control means and/or the deflection control means may be adapted to provide fade-in and fade-out.

The light intensity control means and/or the deflection control means may be adapted to control the intensity of the light beam and/or the velocity of the scanning light beam along a predetermined path as a function of the position of the light beam inside the area of the target surface area.

To provide the normal ablation of tissue, the light intensity control means may be adapted to provide a substantially constant intensity of the light beam and the deflection control means may be adapted to provide a substantially constant velocity of the scanning light beam when the scanning light beam is inside a first part of the target surface area.

If desired, the fade-in and fade-out effect may be provided either by scanning the light beam with a velocity larger than the substantially constant scan velocity within the treatment area of tissue or, by decreasing the output power of the light beam.

The light beam control means may be adapted to control the power-per-area of the light beam when scanned along a predetermined path on a target tissue area to be treated. For example, when ablating tissue it is presently preferred to maintain the power-per-area of the light beam inside a first part of the target tissue area at a substantially constant level.

In order to create the fade-in or fade-out effect, the power-per-area of the light beam when outside a first part of the target tissue area may depend on the distance to the first part of the target tissue area, and it is preferred that the power-per-area of the light beam increases with decreasing distance to the first part of the target tissue area.

Keeping the intensity of the light beam substantially at the constant level as provided inside the first part of the target tissue, fade-in and fade-out may be provided by scanning the light beam with a velocity larger than the substantially constant scanning velocity within the first part of the target tissue area.

Likewise, keeping the velocity of the scanning light beam substantially constant inside the first part of the target tissue, the fade-in and fade-out may be provided by emitting a light beam with a smaller intensity than the substantially constant intensity of light emitted within the first part of the target tissue area.

The light intensity control means and/or the deflection control means may be adapted to provide a varying intensity of the light beam outside the first part of the target surface area. The intensity of the light beam may be varied between a first intensity being substantially identical to the substantially constant intensity in the first part of the target tissue area and a second intensity being an intensity at substantially zero, i.e. no light is emitted from the output of the handpiece or the second intensity may be a low intensity not affecting tissue.

The user interface means may also enable selection of parameters relating to fade-in and fade-out, such as scanning velocity of the output light beam from the apparatus, e.g. the handpiece, in the fade-in or the fade-out area, intensity of the output light beam emitted from the apparatus in the fade-in or the fade-out area, size of fade-in or fade-out areas, shape of fade-in or fade-out areas, etc.

In the case where the light beam is invisible, e.g. utilising an infra red emitter, an ultra violet emitter, etc, a light source generating visible light may be provided for generating a visible light beam that is used to assist the operator by indicating areas towards which the invisible and treating light is directed during scanning. For example, the input connector of the handpiece may be further adapted to connect a second beam-outlet end of a second optical fibre for transmission of a visible light beam to the handpiece. The second optical fibre is preferably properly aligned in the connector in relation to the predetermined path of the visible light. The handpiece may further comprise second deflection means for adjustable deflection of the visible light beam in such a way that the light beam and the visible light beams emitted from the output of the handpiece illuminate substantially the same area of a target surface.

Further, two crossing visible light beams may be emitted from the apparatus or the handpiece, the cross point of the beams indicating the focus point of the light beam. Alternatively, a number of light beams may be emitted from the handpiece, the light beams forming a cone of light, the diameter of the cone at the tissue surface indicating the focus point of the treating light beam.

Preferably, common deflection means are utilised for deflection of all light beams emitted from the apparatus or the handpiece whereby tracking of the light beams are easily accomplished. The deflection means may thus comprise Zinc selenide lenses, as they are transparent for visible light as well as for infrared light.

In order to further assist the operator of the apparatus, the visible light beam may, e.g. between scanning with the light beam, be traversed around at least a part of the circumference of the target surface area thereby indicating the size, shape and position of the target surface area to be traversed with the light beam.

When a polygonal shape of the target surface area has been selected, the visible light beam may, e.g. between scans by the treating beam, be scanned along one edge of the polygon.

Thus, the method may further comprise the step of transmitting a visible light beam towards the target surface area utilising the first deflection means.

The method may further comprise the step of scanning the visible light beam along at least a part of the circumference of the target surface area to be traversed by the light beam.

In order to further assist the operator of the apparatus in keeping a constant distance from the output of the handpiece to the surface of the tissue to be ablated, the handpiece may comprise a distance member connected to the handpiece at the output with fastening means.

As the distance member will touch the patient, it is desirable to insert a new, disinfected member before treatment of a new patient and thus, it is preferred that the fastening means comprises a magnet so that a used distance member can easily be disconnected from the handpiece, e.g. for autoclaving, and so that a new member can easily be connected to the handpiece.

The apparatus according to the present invention may further comprise a processor for control of the apparatus and comprising one or more control means, such as deflection control means, light beam control means, light intensity control means, etc. The processor may further be connected to the user interface means and may be adapted to control the functions of the handpiece in accordance with inputs from the user interface means.

According to a preferred embodiment of the invention the processor means is positioned inside the handpiece.

The processor may comprise a memory, such as an EEPROM, such a flash EEPROM, such as hard disk, etc., for storing of different parameters of scanning patterns and fade-in and fade-out patterns, such as target surface area size, scanning duration, etc. Further the processor means may comprise the tissue parameter storage means for storage of coherent data sets of signal values provided by the detector means at positions along the predetermined path and the respective corresponding positions thereby mapping tissue parameters as a function of stored relative positions along the path.

The apparatus, e.g. in the form of a handpiece may further be provided with a computer interface facilitating reception of scanning pattern parameters generated in a computer and transmitted to the apparatus for storage in the memory. The user interface may be utilised for selection of a specific scan pattern from the set of patterns stored in the memory as previously described. The computer may be any programmable electronic device capable of storing, retrieving and processing data, such as a PC.

It is an important advantage of provision of a processor in the handpiece that signal lines between the handpiece and an external device controlling the handpiece are not needed. This reduces weight of the handpiece with cables connected. Further, electrical noise on control lines is minimised because of reduced lengths of the lines. Still further, control speed is increased as capacitance of a short line is small.

Various scan patterns may be created on a PC and be downloaded to the memory of the handpiece. The patterns may be stored in the form of a table of parameters defining number of lines, length of lines, distance between lines, start and end points of fade-in and fade-out of each line, points of turn on and turn off of the scanning light beam, etc of each scan pattern stored.

A scan pattern box may be provided, containing a processor, a memory and interface means for storage of scan patterns generated, e.g. on a PC and transmitted to the box through the interface means for storage in the memory. The interface means of the box and the computer interface of a handpiece may be interconnected and the various scan patterns stored in the box may be transferred to the memory of the handpiece whereby scan patterns created at a single PC may be distributed to a plurality of handpieces that may be situated remotely from the PC.

BRIEF DESCRIPTION OF THE DRAWINGS

In the following, a preferred embodiment of a cosmetic tissue treatment apparatus comprising detector means will be described with reference to the drawings, wherein.

DETAILED DESCRIPTION OF THE DRAWINGS

Figure 1:
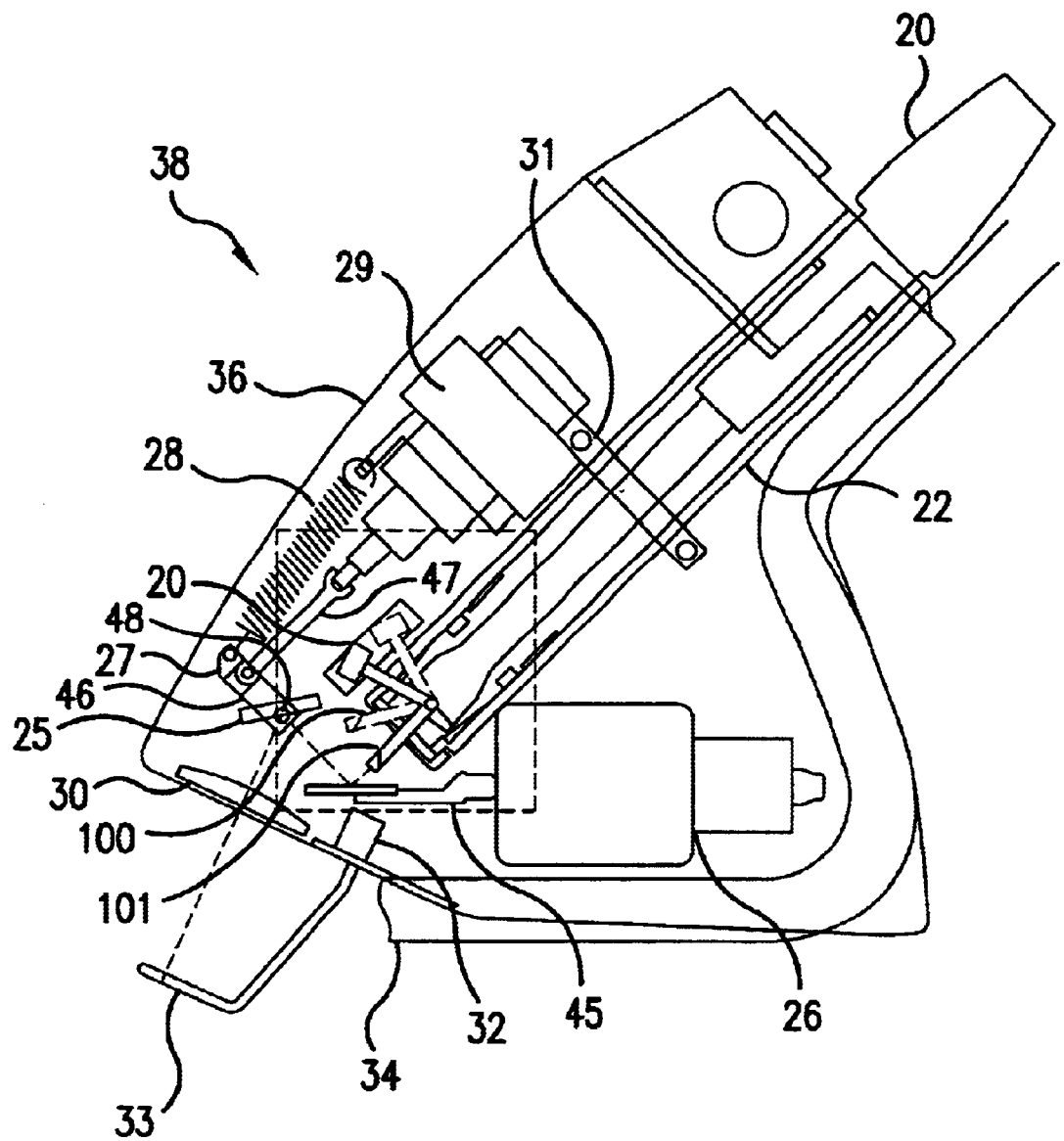
FIG. 1 shows a cross section of a handpiece according to the present invention.

FIG. 1 shows a handpiece 38 of an apparatus for tissue treatment according to the present invention. A cable 1 (not shown) is connected to the handpiece 38 at a fibre inlet member 20, and is guided through a tube 22 which is held in place in the handpiece 38 by the holding and heat distributing means 31. The fibre inlet member 20 also serves as a cable-protecting sleeve. The cable comprises an optical fibre 2 that is positioned at the centre of the cable 1. The optical fibre 2 is made of silver chloride and silver bromide (silver halide), which is especially designed for transmission of light at a wavelength of app. 10.6 $\mu$m. The cable 1 further comprises two glass fibres 6, 7. The two glass fibres 6, 7 have a small NA (numerical aperture) designed for propagation of visible light at a wavelength of app. 650 nm.

A treating light beam emitted by a $CO_2$ laser is transmitted through the optical fibre 2 and guiding light beams from two diode lasers are transmitted through the glass fibres 6, 7, respectively.

Figure 2:
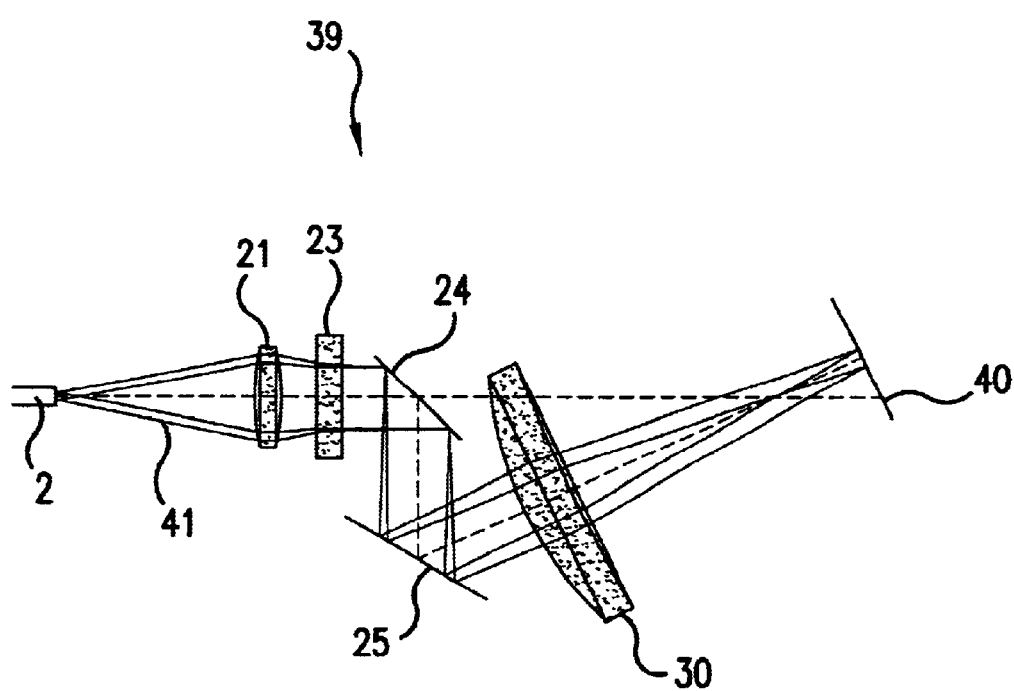
FIG. 2 shows the lens system of the handpiece shown in FIG. 1 in treatment mode in greater detail.

The light beams transmitted in the optical fibre 2 and the two glass fibres 6, 7, respectively, are radiated from the respective beam-outlet ends of the fibres 2, 6, 7 through a lens system 39—shown in greater detail in FIG. 2—towards an object, e.g. a human tissue surface. Each of the beam-outlet ends of the fibres 2, 6, 7 is positioned at a distance appropriate for the focusing lens 21 to focus the light from the fibre in question 2, 6, 7 on the object.

In FIG. 2, the lens system 39 is shown in greater detail. The treating and guiding light beams radiated from the beam-outlet ends of the fibres 2, 6, 7 are focused by the first focusing lens 21 and collimated by the collimating lens 23. The collimated light beams are transmitted from the collimating lens 23 via deflection means comprising a first mirror 24 and a second mirror 25 to a second focusing lens 30 which focuses the light beams on the target 40, which e.g. can be the facial tissue of a human being. The distance between the focusing lens 30 and the focus plane at the object 40 is preferably approx. 27 mm.

Reverting to FIG. 1, the first deflection means also constitutes the second deflection means and comprises the first mirror 24 that is mounted on the first deflection means that also constitutes the second deflection means and comprises a galvanometer 26 with an indicator 45 and positioned in the handpiece 38. When an electric current is driven through the coil of the galvanometer 26, the magnetic field generated by the current will make the indicator 45 rotate around the longitudinal axis of the indicator 45. The first mirror 24 will thereby be rotated, and the light beams will be deflected at an angle twice the angle rotated by the mirror 24 in relation to the light beam. The positioning resolution of the galvanometer 26 is limited by the electronic deflection control means controlling the galvanometer 26 to 255 positions.

The first deflection means also comprise the second mirror 25 mounted on an arm 46 actuated by a linear actuator 29 comprised by the first deflection means. When the linear actuator 29 activates the actuator arm 47, the arm 46, and thereby the second mirror 25, is rotated around the shaft 48. A spring 28 is connected to one end of the arm 46 and to a non-moving part of the linear actuator 29 in the other end so as to prevent wobble around the shaft 48. When the second mirror 25 is rotated around the shaft 48, the light incident on the second mirror 25 is deflected an angle that is twice the angle rotated by the mirror 25. The linear actuator 29 may be controlled by applying a sequence of pulses across the terminals (not shown) of the actuator 29. The positioning resolution of the linear actuator is discrete and limited to a maximum number of steps of approx. 200.

The optics of the apparatus limits the possible scan area to approx. 10*10 mm, corresponding to an angular displacement of the mirror 24 of approx. ±8θ and an angular displacement of the mirror 25 of approx. ±5θ, even though the maximum movement of the mirror 24 is approx. ±11θ and the maximum movement of the mirror 25 is approx. ±10θ. The extra possible movement which is not used during scanning is used during start-up of the system to ensure accurate and reliable speed before the treatment scan is started.

By controlling the current to the coil of the galvanometer 26 and the pulse sequence applied across the terminals of the linear actuator 29, the direction of light beams emitted from the focusing lens 30 towards the target 40 can be controlled. It is thus possible to create different kinds of scan patterns of the light beam, such as rectangular or circular scan patterns.

An arm 100 with a mirror 101 is rotatably mounted for rotation by a solenoid 109. In one position the mirror 101 is positioned in the beam path of the treating laser light beam when the optical system is in a sensing mode as explained further below.

Figure 3:
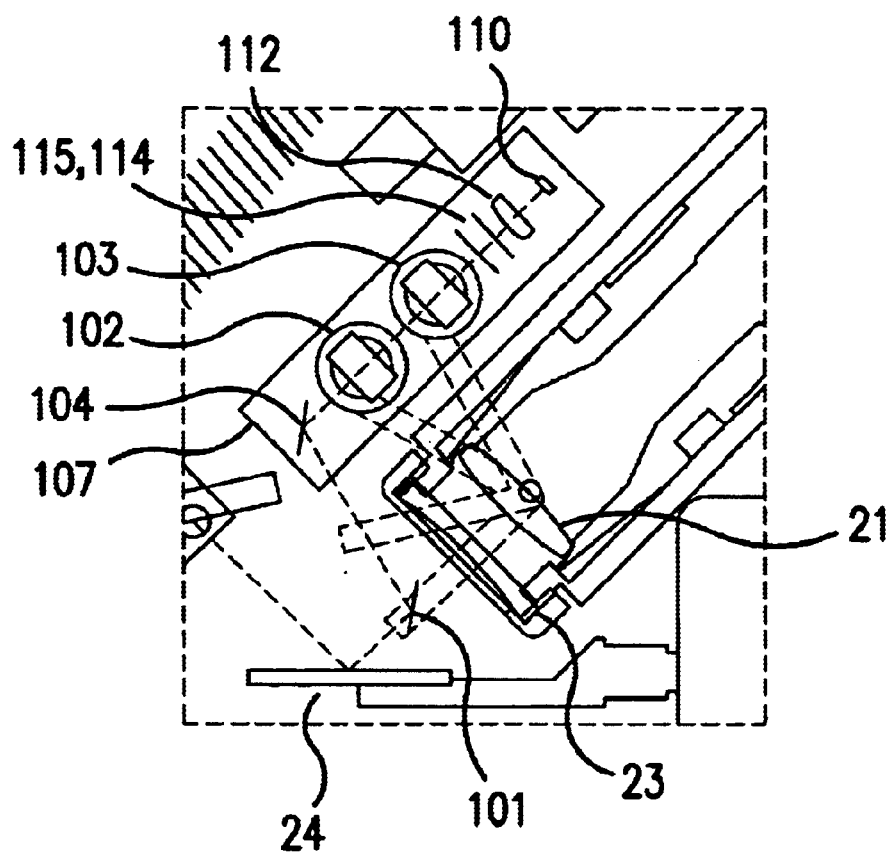
FIG. 3 shows the dashed area of FIG. 1, the detector means in more detail.

In FIG. 3, the part of the handpiece defined by the dashed line in FIG. 1 comprising the detector means is shown in greater detail. The detector means comprises a detector 110 and two light sources 102, 103 mounted in a holder for optical elements. The detector means further comprises an adjustable mirror 101. In sensing mode, the adjustable mirror 101 is positioned so as to transmit illuminating light beams emitted from the light sources 102, 103 mounted in the optical holder 107 via the fixed mirror 104 to the first mirror 24, the second mirror 25, and the second focusing lens 30 which focuses the light beams on the target 40. Likewise, reflected sensing beams reflected from the target 40 are directed back to the detector via the focusing lens 30 and the adjustable mirrors 24, 25. From the mirror 101 at the rotating arm 100 the reflected sensing beams are directed via the fixed mirror 104 towards the detector 110 for intensity detection.

Figure 4:
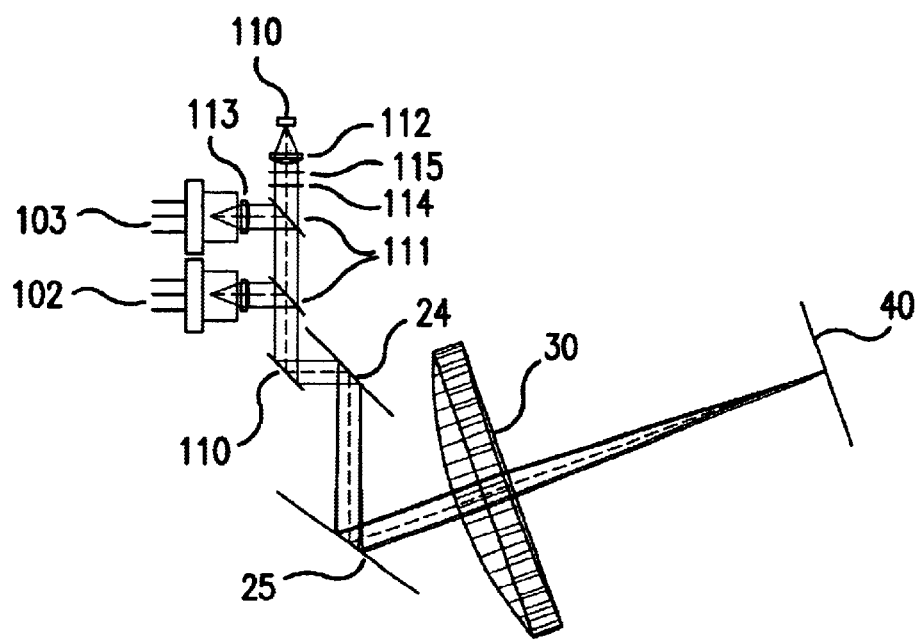
FIG. 4 shows detector means of the handpiece shown in FIG. 1 in sensing mode in greater detail.

FIG. 4 shows the detector means schematically in greater detail. For simplicity the mirror 104 is not shown in FIG. 4. The light sources 102, 103 are laser diodes which emit light at different wavelengths. Each of the emitted illuminating light beams is collimated by respective collimating lenses 113 and is directed by beamsplitters 111 towards the adjustable mirror 101 and by the mirror 101, each of the illuminating light beams is directed to the target 40 via mirror 24, mirror 25 and focusing lens 30. Thus, the output optics is used to scan both the illuminating light beams and the treating and guiding light beams emitted from the beam-outlet end of the fibres. The sensing beams reflected from the target 40 propagate along the same path back to the beam-splitters 111. The polarisation of the light beams is changed when the light is reflected from the target 40, and since the transmittance of the beamsplitters 111 are dependent on the polarisation of the incident light beam the reflected sensing light beams reflected from the target 40 are transmitted through the beamsplitters, without reflection. A polarisation filter 114 and a blockout filter 115 is positioned in front of the detector 110 to increase signal to noise ratio. A third focusing lens 112 focuses incident beams at the detector. To determine the colour of tissue at the target 40 a red and a green light beam from respective light sources 102, 103 are alternately directed towards the target 40. The reflection of the red and the green light beams, respectively, from the target 40 are directed to the detector by the deflection means and are detected at the detector 110. The differences in the reflected light from light sources 102, 103 are calculated and a tissue parameter, i.e. the colour, of the tissue to be treated is thereby determined. Depending upon the tissue parameter to be determined, it is of course envisaged that the illuminating beams may be visible light beams of any colour, or it may be ultra violet light beams, or it may be infrared light beams.

As shown in FIG. 1, the optics and electronics of the handpiece 38 are protected by a plastic housing 36 provided in an ergonomical shape. An air tube 34 may be positioned on the handpiece 38 for providing suction of air from in front of the optics of the handpiece 38 in order to absorb any material ablated from the tissue of the object being treated with the apparatus of the present invention.

The guiding light beams from the two glass fibres 6, 7 transmitted from the cable 1 through the optics of the handpiece and to the object, intersect at a distance equal to the focal length of the focusing lens 30, i.e. at the distance where the light from the $CO_2$ laser is focused. This is the distance at which the handpiece should be held from the object to obtain the best treatment result, and the intersection of the two visible guiding light beams assists the operator in maintaining a correct distance to the tissue surface.

Because of the importance of keeping the $CO_2$ focal point on the tissue surface, the presently preferred embodiment of the handpiece 38 shown in FIG. 1 further comprises a magnetic distance member 33 connected to the handpiece 38 with fastening means 32. The fastening means may comprise a magnet whereby the distance member 33 can be attached to or removed from the handpiece 38 in an easy and convenient way.

The embodiment of the invention shown in FIGS. 1–5 may further comprise an infrared light detector for determination of the temperature of the target.

Furthermore, the arm 100 with mirror 101 may be replaced by a beamsplitter enabling simultaneous determination of tissue parameters and treatment of tissue.

Figure 5:
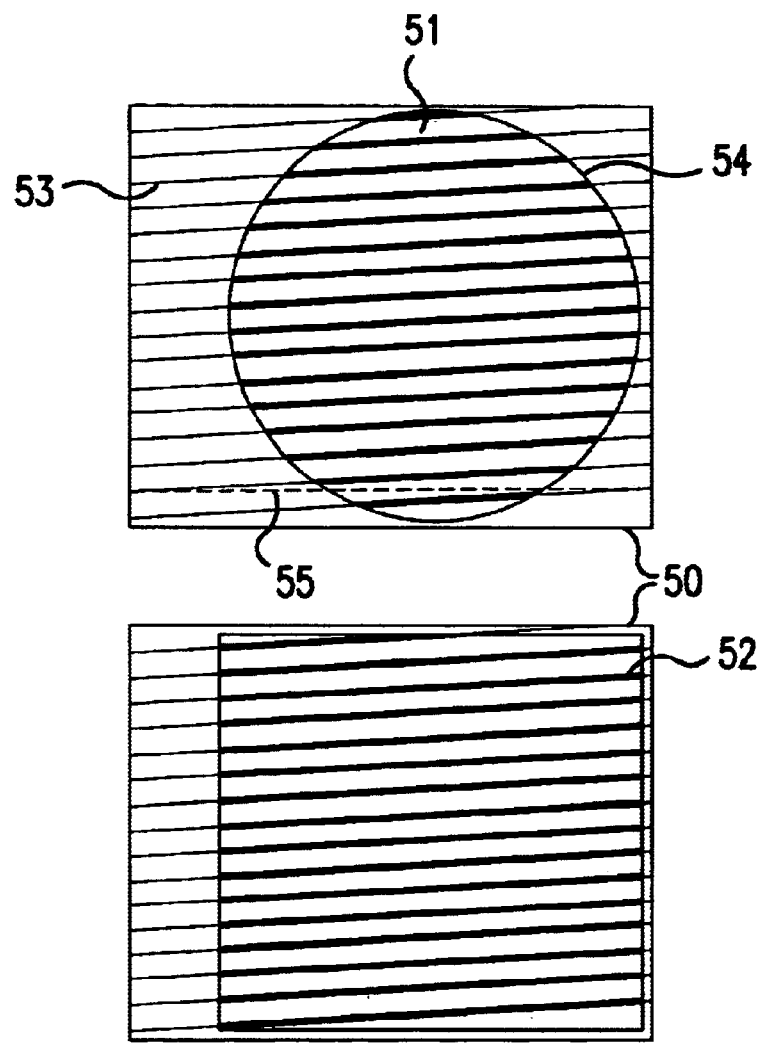
FIG. 5 shows a circular and a quadratic scan area.

In FIG. 5, a quadratic scan area 52 and a circular scan area 51 are shown. The actual laser scan area is indicated by reference numeral 50, but only the scan areas 51, 52 are used for tissue treatment. The thin lines 53 and the thick lines 54 indicate the scan path of the laser beam. The thin lines 53 indicate parts of the scan where the laser is turned off, while the thick lines 54 indicate parts of the scan where the laser is turned on.

The scan is performed as a slow forward/fast returnscan (a TV-scan, but without interlacing). The scan starts at the lower left corner of the actual scan area 50. The laser beam is moved towards the right, and when the laser beam enters the tissue treatment scan area 51 or 52, the laser is turned on. When the laser beam leaves the tissue treatment scan area 51 or 52, the laser is turned off, and when the laser beam reaches the right edge of the actual scan area 50, the beam is quickly retraced or moved to the left edge of the actual scan area 50, and the laser beam is moved along the next scan line positioned immediately above the previously scanned line.

In stead of turning the laser on and off, the speed of the movement of the laser beam may be increased to a speed sufficiently high for the laser beam not to ablate the tissue surface.

The fast movement (trace and retrace) of the laser beam between the right and left edges of the actual scan area 50, is accomplished by controlling the galvanometer 26. In order to let the mirror 24 settle after the fast movement from the right edge of the actual scan area 50 to the left edge, the first part of the scan line is not used for tissue treatment. The slower movement of the laser beam from the bottom to the top of the actual scan area 50 is accomplished by controlling the linear actuator 29 in a constant movement of the mirror 25.

A quadratic scan area of approx. $9^*9$ mm comprises 30 scan lines, and the max. scanning speed is app. 300 mm/s.

The operator of the apparatus controls the scanning using a pedal. When the pedal is activated, scan starts. After finishing the scanning, the $CO_2$ laser is turned off, and the visible guiding light beam scans around at least a part of the circumference of the scan area 51 or 52 thereby indicating the size, shape and position of the scanned area 51 or 52. The operator may now move the handpiece and select a new scan area, e.g. a scan area abutting the area just scanned, and when the operator releases the pedal and again activates it, a new scanning will take place. In this way, the operator of the apparatus may easily scan larger areas of the tissue by successively scanning neighbouring areas.

Figure 6:
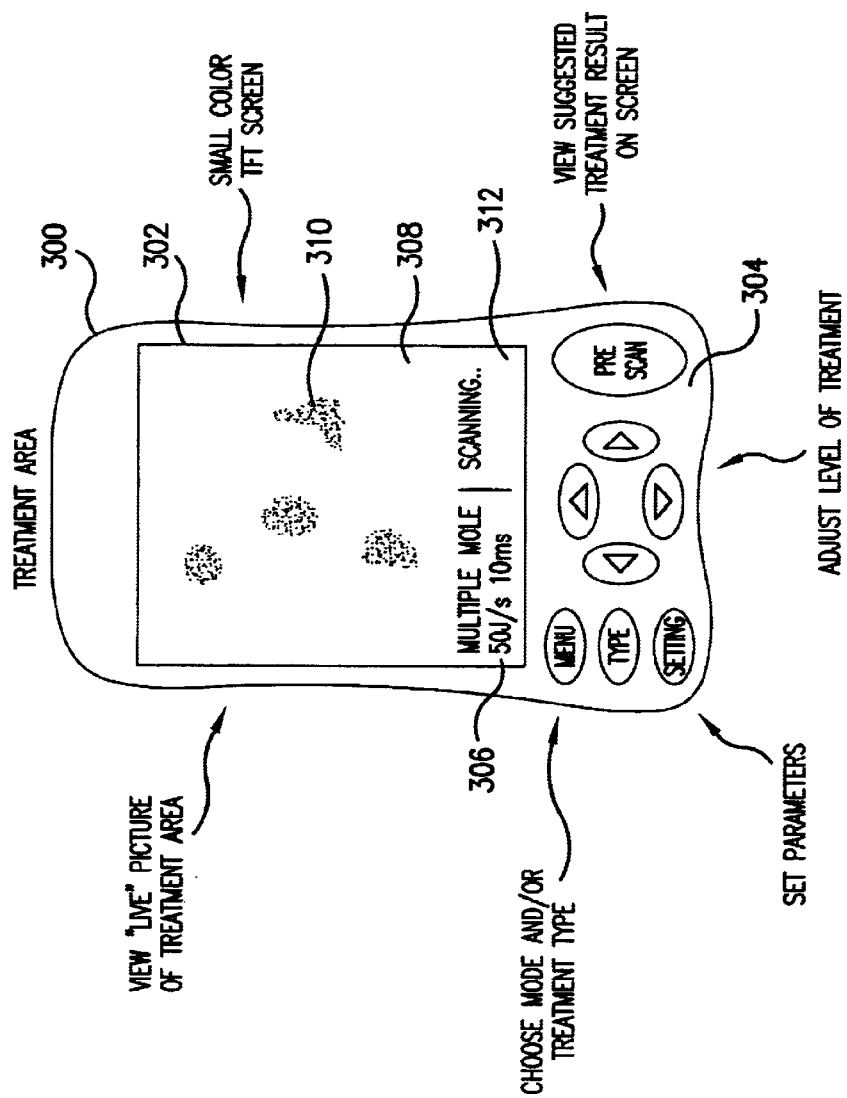
FIG. 6 shows a user interface means comprising a display according to the invention.

FIG. 6 shows user interface means 300 of the apparatus positioned at the handpiece 38. The user interface means 300 comprises a small colour TFT display 302 and various keys 304 for user selection of operational parameters 306 of the apparatus. In the example illustrated, the handpiece 38 is positioned on tissue of a patient with moles 310 to be removed. First, the viewing area 50 of the handpiece 38 is scanned without treatment whereby the colours of the tissue within the viewing area 50 is detected as described previously and stored in the tissue parameter memory. The corresponding colour map 308 is displayed on the TFT display 302. The handpiece 38 may also comprise a video camera (163, FIG. 9) such as a CCD camera, and the viewing area 50 as recorded by the video camera may be displayed on the TFT display 302.

The handpiece 38 may also comprise a processor 141 for processing the image displayed on the TFT display 302 for recognition of tissue features 310, such as moles. In this example, moles are distinguished from surrounding tissue by their distinguishing colour. Thus an average value for the recorded intensity of the distinguishing colour may be calculated for the viewing area 50 and may be used as a threshold value. Tissue areas with recorded intensities of the distinguishing colour above the threshold value is considered to constitute mole tissue. The processor 141 may modify the displayed map to enhance the display of moles. As previously described, the operator may select some moles (e.g. by touching the mapped moles on the TFT display) for treatment leaving the remaining moles untreated. Based on the recorded tissue parameters and selected areas for treatment, the processor 141 may calculate the parameters 306 of the treating light beam, for example wavelength, output power, duty cycle, etc, or, the parameters may be looked up in a database. The calculated parameters 306 may be displayed on the TFT display 302 and modified by the operator using the keys 304. Having selected the desired parameters and areas to be treated, the operator presses a footswitch for activating a second scan of the viewing area 50 during which the treatment laser is turned on when the light beam impinges on a mole selected for treatment. During treatment, the displayed map is compared to the map displayed during parameter and treatment area selection and any movement of the handpiece between selection and treatment is appropriately compensated for.

The handpiece 38 may further comprise an infrared detector optically positioned in the same light path as the light detector 110 so that a temperature profile of the viewing area 50 may be recorded. A map of the temperature profile may be displayed on the TFT display 302 facilitating analysis and quality control of the treatment. The temperature map may be overlaid the previously described colour map 308. Based on the analysis, the operator may decide to adjust the light beam parameters 306 and/or to repeat the treatment of the viewing area with the same or different parameter values. The user may select to store treatment parameter values in a memory for reuse on the next tissue area to be treated.

The temperature may thus also be recorded and displayed on the TFT display 302 during treatment so that the user can control the treatment during treatment. This is particularly interesting when treating using large pulse widths, such as when removing hairs.

The user interface means 300 may be adapted to select operational parameters of the apparatus, the keys 304 and the display area 312 co-operating for selection of the parameter. The keys may be used to navigate through a menu structure whereby various operational parameters may be displayed sequentially in response to an activation key sequence in any conventional manner as is well known to a person skilled in the art of user interface means comprising keys and a display.

Figure 7:
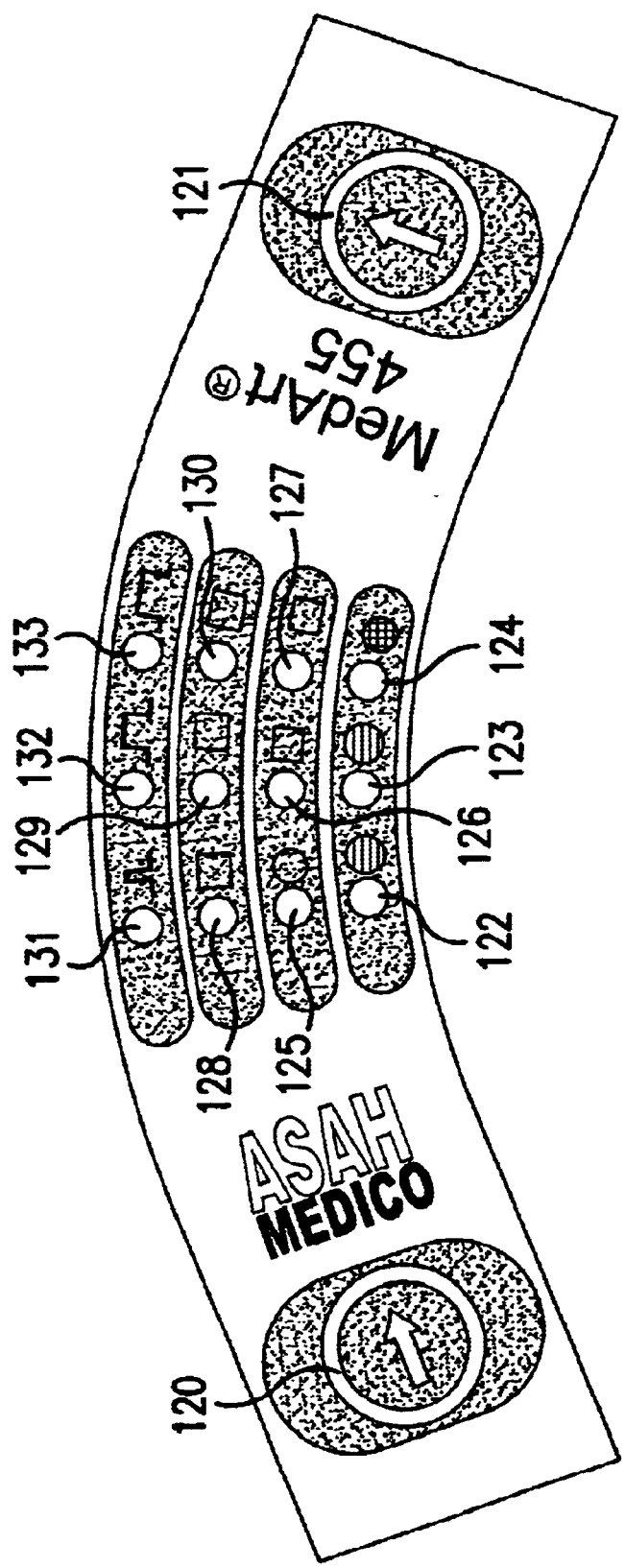
FIG. 7 shows an unfolded wiev of an alternative user interface means provided at the handpiece.

An alternative user interface means is shown in FIG. 7. The user interface means is adapted to be positioned on the handpiece and is shown unfolded.

The user interface means comprise two push buttons 120, 121 and twelve light emitting diodes arranged in four rows, each row comprising three diodes.

Each row is used to indicate selection of a parameter value of a corresponding parameter type.

The row comprising diodes 122, 123, and 124 indicates selection of shape of the scan pattern. Diode 122 is turned on when a circular scan pattern is selected, diode 123 is turned on when a quadratic scan pattern is selected and diode 124 is turned on when a line scan pattern is selected.

The row comprising diodes 125, 126, and 127 indicates selection of fade-in and fade-out patterns. Diode 125 is turned on when a pattern with fade-in from the left is selected, diode 126 is turned on when a pattern with fade-in from the left and fade out to the right is selected, and diode 127 is turned on when a pattern with fade-in and fade-out, respectively, from both sides as well as from top and bottom of the scan pattern is selected.

The row comprising diodes 128, 129, and 130 indicates selection of the size of the scan pattern. The diode 128 is turned on when a small scan pattern is selected, diode 129 is turned on when a medium sized scan pattern is selected, and diode 130 is turned on when a large scan pattern is selected.

The row comprising diodes 131,132, and 133 indicates scan velocity. Diode 131 is turned on when a high scan velocity is selected, diode 132 is turned on when a medium scan velocity is selected, and diode 133 is turned on when a low scan velocity is selected.

Depression of the push button 121 causes one of the light diodes to start flashing in one row indicating that parameter values of the type corresponding to that row can be selected. By depressing push button 121 once more, a light diode in another row will start flashing and thus, by repeatedly depressing push button 121, parameter values of each type indicated by the user interface means may be selected.

In the row in which a light diode is flashing, the desired parameter value may be selected by depressing the push button 120 until the diode indicating selection of the desired parameter value is flashing.

Thus, selection of scan area parameter values of the handpiece may be done immediately prior to scanning of the treatment area. Selection is very simple and does not require utilization of an external computer for programming of desired scan patterns.

Using either user interface means or a combination thereof, selectable operational parameters may comprise shape of the scan pattern, such as a circular shape, a rectangular shape, a triangular shape, etc, fade-in and fade-out patterns, size of the scan pattern, number of scan lines within the selected scan area, scan velocity, peak power of the treating light beam, duty cycle of the treating light beam (including 100% duty cycle), etc.

For example, when a quadratic scan pattern is selected, the scan area may be approx. $9^*9$ mm, $6{,}5–7$ mm$^*$ $6{,}5–7$ mm, such as approx. $6^*6$ mm, or $3{,}5–4$ mm$^*$ $3{,}5–4$ mm, such as approx. $3^*3$ mm, if the scan pattern is circular, the diameter of the circle may be approx. 9 mm, such as 10 mm, approx. 6 mm, such as 6,5–7 mm, or approx. 3 mm, such as 3,5–4 mm, and if the scan pattern is a line, the length of the line may be approx. 9 mm, such as 10 mm, approx. 6 mm, such as 6,5–7 mm, or approx. 3 mm, such as 3,5–4 mm.

In the example above, the number of scan lines in a quadratic or circular scan may be approx. 10 scan lines per scan area if the scan size is small, or the number of scan lines may be approx. 20 scan lines per scan area if the scan size is medium, or the number of scan lines may be approx. 30 scan lines per scan area if the scan size is large.

Thus, the time to complete a scan depends on the scan size and the scan speed. If for example the scan speed is high the time to complete a scan is approx. 0.15 sec if the scan size is small, approx. 0.5 sec if the scan size is medium, and approx. 1 sec if the scan size is large. If the scan speed is medium the time to complete a scan is approx. 0.2 sec if the scan size is small, and approx. 0.7 sec if the scan size is medium, and approx. 1.5 sec if the scan size is large. If then the scan speed is slow the time to complete a scan is approx. 0.3 sec if the scan size is small, and approx. 0.9 sec if the scan size is medium, and approx. 2 sec if the scan size is large.

Depending on the application of the handpiece, the high velocity may be equal to 350 mm/s. At the high velocity approx. 5 J/cm$^2$ is supplied to the scanned area. The medium velocity may be equal to 225 mm/s at which velocity approx. 8 J/cm$^2$ is supplied to the scanned area. The low velocity may be equal to 175 mm/s at which velocity approx. 10 J/cm$^2$ is supplied to the scanned area.

A larger scan area may also be used, for example a scan area of $30–50^*30–50$ mm, such as approx. $50^*50$ mm, approx. $45^*45$ mm, approx. $40^*40$ mm, or approx. $30^*30$ mm, $10–30^*10–30$ mm. such as approx. $30^*30$ mm, approx. $25^*25$ mm, approx. $20^*20$ mm, approx. $15^*15$ mm, approx.

10*10 mm, may be used whereby larger tissue areas may be treated without having to move the handpiece.

When scanning on different types of tissue, it is preferred to adjust the scan speed of the light beam in stead of adjusting the output power of the light beam. When scanning on tissue with a low absorption of light, such as dry skin, it is preferred to generate a high power density on the tissue, and a low speed should be selected. When scanning on tissue with an average absorption of light, a medium scan speed should be selected, and when scanning on tissue with a high absorption of light, a high scan speed should be selected.

The selectable operational parameters may be stored in the memory of the handpiece. The weight of the cables and thereby of the handpiece is reduced because there is no need for cables connecting the handpiece to an external controller. Sets of scan pattern parameters, i.e. shape and size, fade-in and fade-out, number of lines, etc, may also be stored in the memory of the handpiece facilitating an easy to learn and understand user operation. New scan patterns may be downloaded to the memory of the handpiece through its computer interface. When the desired scan patterns have been downloaded, the computer interface can be disconnected from the source of sets of scan pattern parameters and the handpiece will be ready for use.

As already described, the selected operational parameters may be modified before or during treatment in accordance with detected tissue parameters and in accordance with areas selected for treatment.

Figure 8:
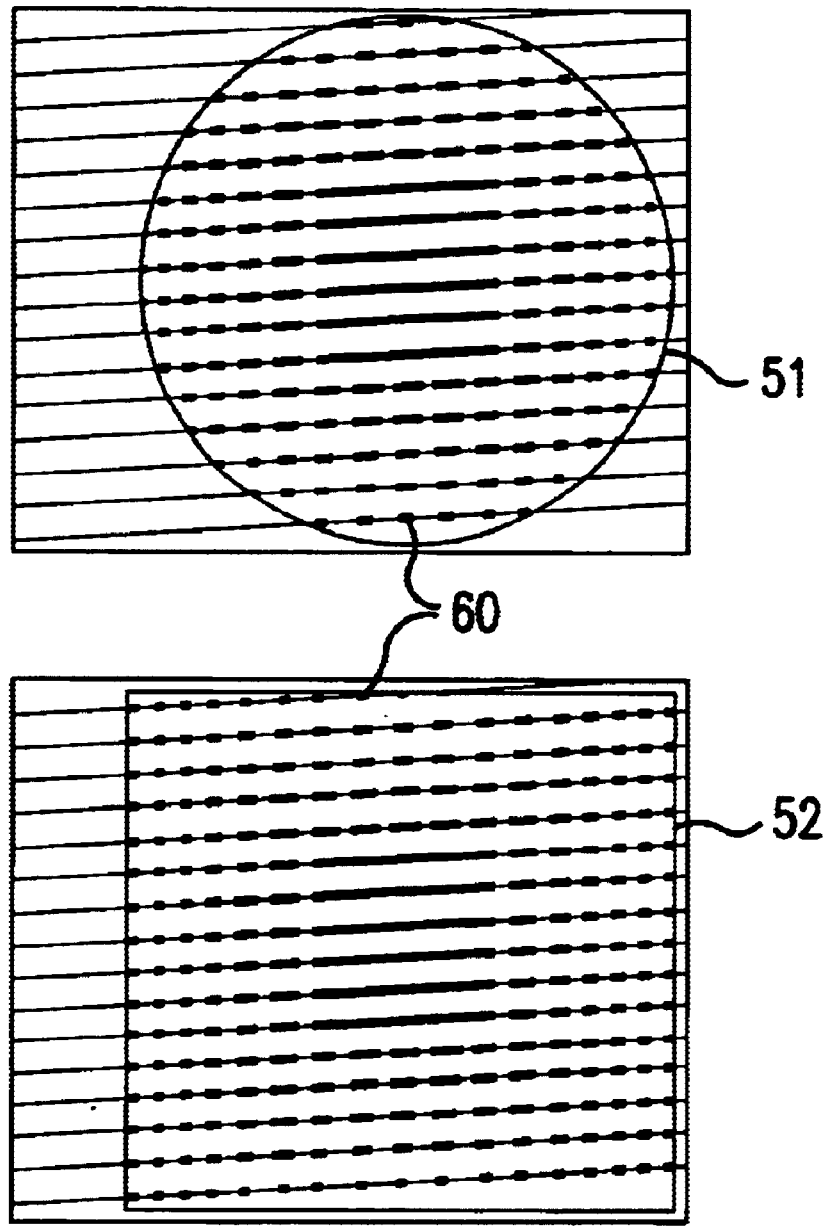
FIG. 8 shows scan patterns for treatment of a single mole.

FIG. 8 shows a viewing area with a single mole. The mole is treated with a quadratic scan area 52 or a circular scan area 51 with four-sided fade-out intensity scan lines 60.

Utilisation of fade-in and fade-out intensity scan lines 60 creates a smooth transition from an non-ablated area of the tissue to an ablated area.

The user may select the size and shape of the fade-in and fade-out scan areas.

It should be understood that a fade-in or a fade-out effect may be accomplished by gradually increasing or decreasing the intensity of the laser light, respectively, or by decreasing or increasing the speed of the movement of the laser beam, respectively.

Figure 9:
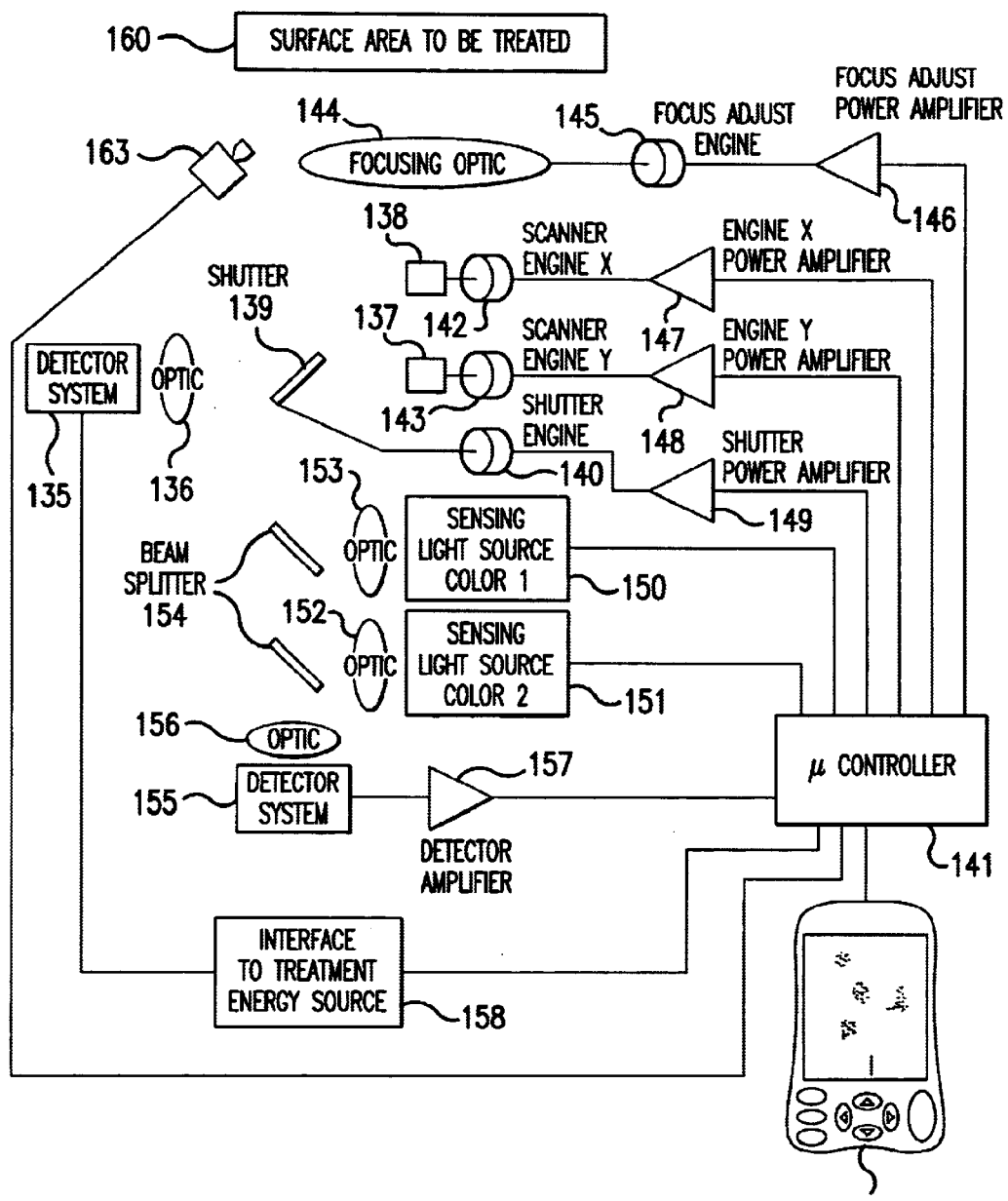
FIG. 9 shows a schematic diagram of the apparatus.

FIG. 9 shows a schematic diagram of a handpiece according to the invention. A treatment light source 135, such as a laser, emits a treating light beam (not shown). The light beam propagates via optics 136 and adjustable mirrors 137, 138 towards the surface to be treated 160. Scanner engine X 142 and scanner engine Y 143 controls the respective mirrors. Thus, the first deflection means comprises the adjustable mirrors 137, 138 and the scanner engines X and Y 142, 143. A shutter 139 is provided in the path of the light beam to prevent the light beam from being irradiated towards the surface to be treated 160. The shutter is controlled via shutter engine 140 by processor 141. To ensure focusing of the light beam at the surface area to be treated 160 adjustable focusing optics 144 is positioned in the path of the light beam. The focusing optics is adjusted via the focus adjust engine 145. Power amplifiers 146, 147, 148, 149 are provided for engines 145, 142, 143 and 140, respectively, for amplification of control signals. The processor 141 comprises the focus control means, the first deflection control means and the shutter control means.

Two light sources 150,151 are provided for directing illuminating light beams through optics 152, 153 and via beamsplitters 154 towards the surface area to be treated 160. A detector means 155 comprising the detector detects the light reflected from the surface area 160 and directed to the detector means 155 via optics 156. The detected signals are transferred to the processor 141 via a detector amplifier 157. The processor 141 further comprises storage means for storage of coherent data sets of signal values provided by the detector means at positions along the path to be scanned by the treating light beam and the respective corresponding positions along the path so that tissue parameters may be mapped as a function of stored relative positions along the path, and light beam control means for controlling parameters of the light beam in response to the detected tissue parameters. Interface means 158 are provided to control parameters of the treating light beam emitted by the light source 135 on the basis of the detected tissue parameters.

The handpiece may also include a video camera 163, connected to processor 141 for receiving images recorded by the video camera.

In an apparatus further comprising a detector array and array optics for forming an image of the target area, the processor 141 may further comprise image processing means for processing the output signals from the detector array.

In the apparatus shown schematically on the figure, the first and second deflection means and the first and second deflection control means are identical.

Further, user interface means 300 are provided comprising the TFT display 302 and keys 304.

Figure 10:
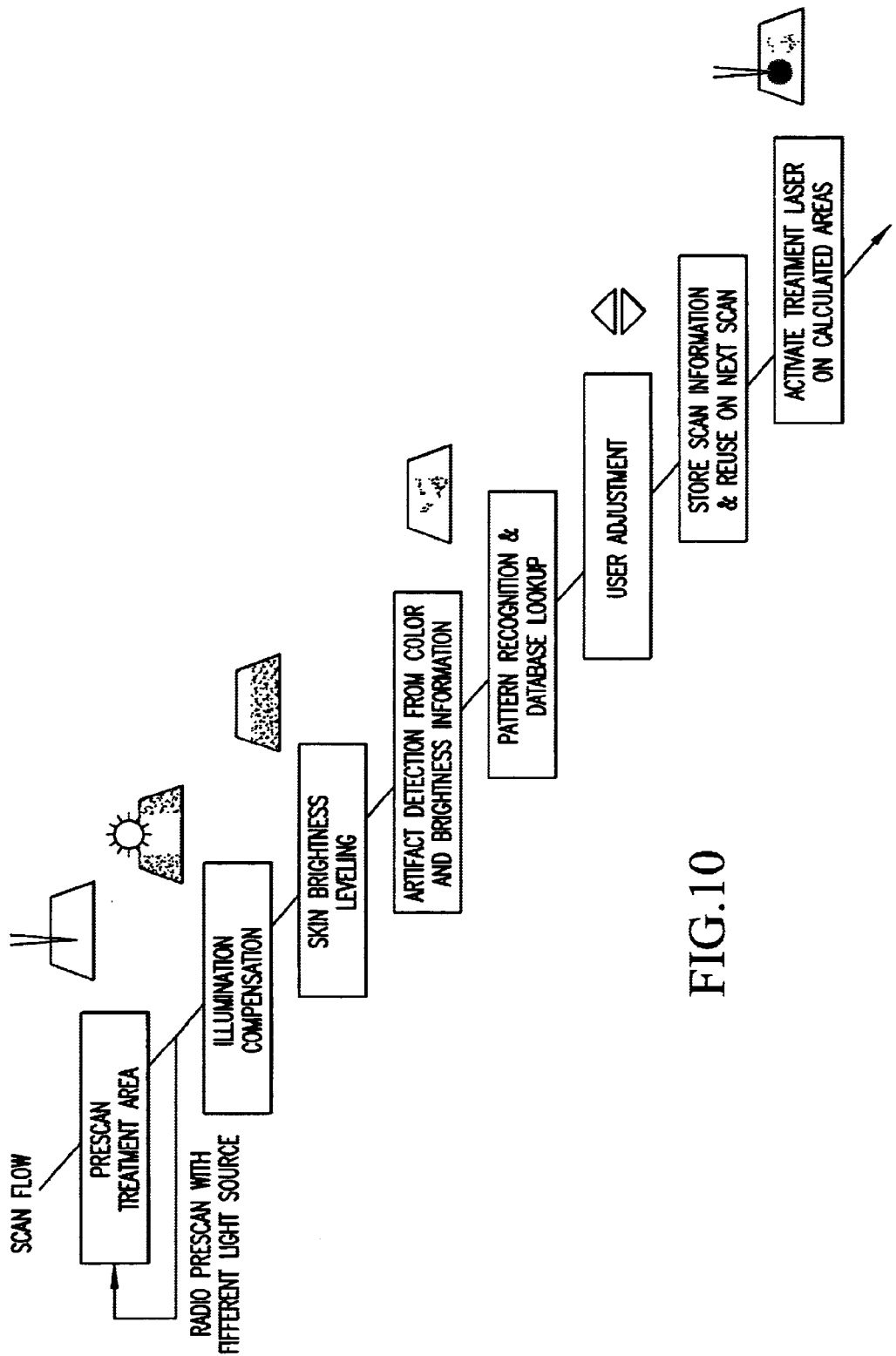
FIG. 10 shows a flow chart of the operation of the apparatus according to the invention, FIG. 11. shows a flow chart of the operation of an apparatus provided with the user interface shown at FIG. 7.

FIG. 10 shows a flow chart illustrating an example of operation of the apparatus.

When the system is in a service mode an external unit may take over the control of the handpiece from the handpiece processor by taking control of the serial IIC bus. The handpiece processor checks whether an external computer is connected to the bus and if so control of the bus is transferred to the external computer. This may be useful when testing and adjusting the handpiece and when reprogramming the scanner.

Figure 11:
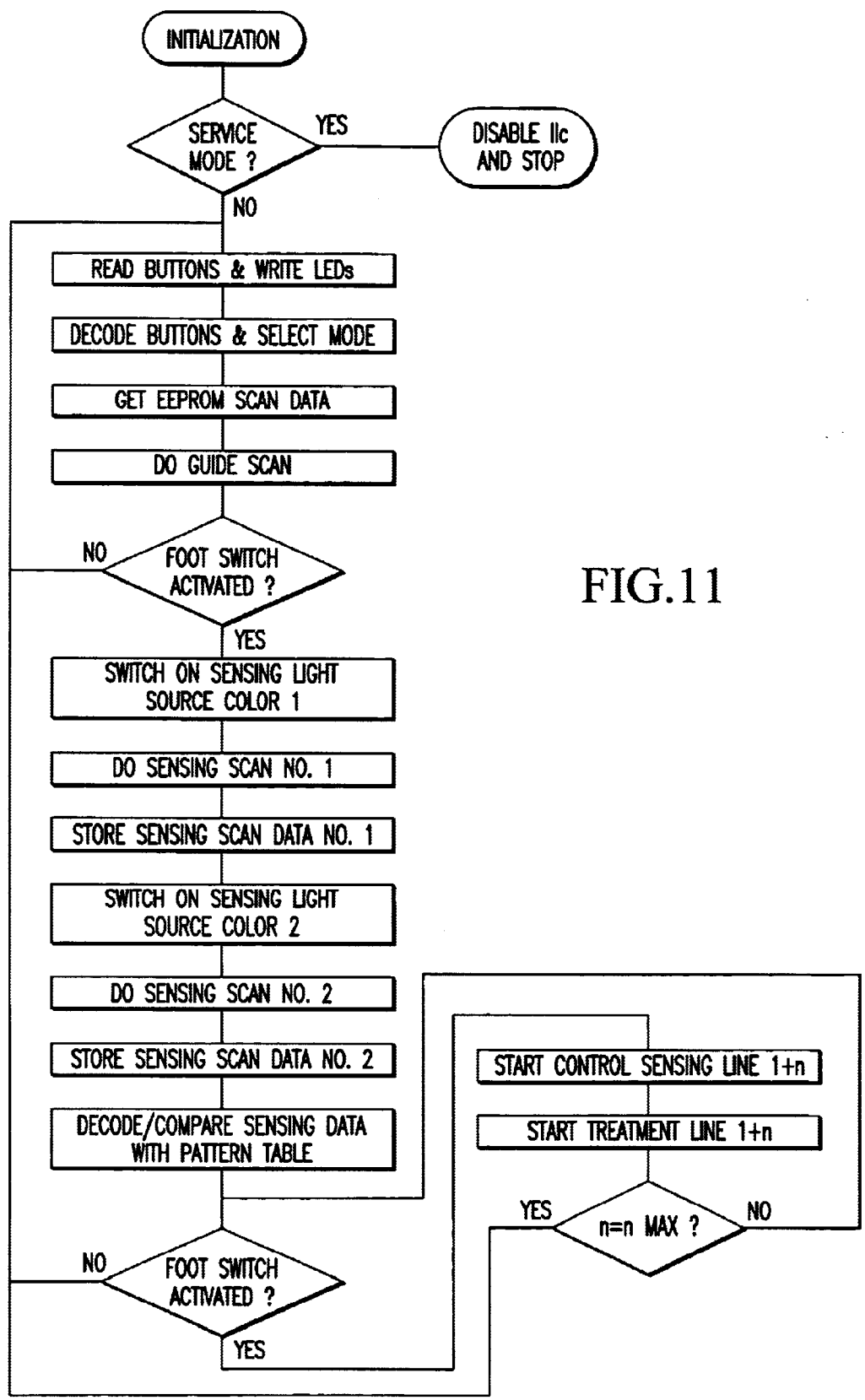

FIG. 11 shows a flow chart illustrates processor operation before the treatment scan is started when a user interface as shown in FIG. 7 is applied.

In the illustrated processor operation two sensing light beams are used and the light reflected from each of these is detected. The scan is performed as a line by line scan.

Processor operation starts in step 165 where the processor is initialized. Hereafter in step 166, the processor checks if the handpiece is in a service mode. If so, the bus IIC, which reads and writes the outputs from the microprocessor is disabled in step 167. If not, in step 168 activation of the push buttons of the user interface means are detected and the light emitting diodes are turned on and off accordingly as previously described. In step 169, the parameter value selections are recorded and the corresponding scan pattern is selected. In step 170, the processor gets data from the EEPROM and perform a guide scan in step 171, i.e. the visible light beam traverses the circumference of the scan pattern or a part thereof as previously described.

In step 172, the processor checks if the foot pedal is depressed or activated. If not activated, the process is repeated from step 168. If the foot pedal is activated then the first sensing light source 151 is switched on in step 173 and in step 174, the sensing light scans the area to be treated along a predetermined path. In step 175, the data collected during the sensing scan is stored. In step 176, the second sensing light beam is turned on and in step 177, a second sensing scan is performed. In step 178, the data collected during the second sensing scan is stored. In step 179, the stored sensing data are decoded and compared with a pattern table. In step 180, the processor checks if the foot pedal is depressed or activated. If not activated the process is repeated from step 168. If the foot pedal is activated then a control sensing scan is initiated from line 1+n in step 181, and the treatment scan is initiated in step 182 at line 1+n, where n is an integer. In step 183, it is controlled whether n is equal to a predetermined n MAX. If not the process is repeated from step 180, if n=n MAX, a new scan may be initiated from step 168.

When the system is in service mode an external unit may take over the control of the handpiece from the handpiece processor by taking control of the serial IIC bus. The handpiece processor checks whether an external computer is connected to the bus and if so control of the bus is transferred to the external computer. This may be useful when testing and adjusting the handpiece and when reprogramming the scanner.

Figure 12:
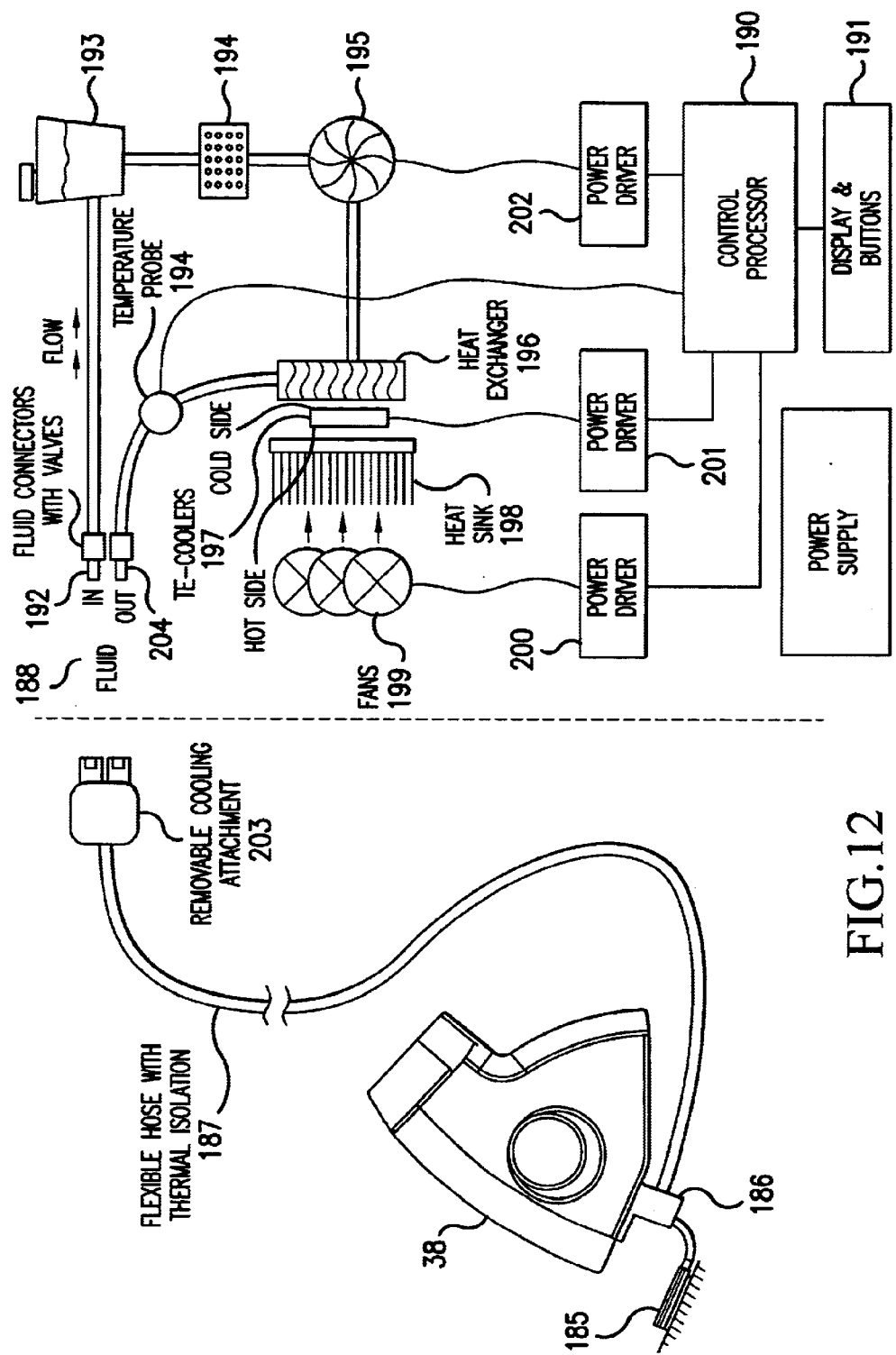
FIG. 12 shows a handpiece according to an embodiment of the present invention wherein a cooling member for cooling of the tissue to be treated is provided.

FIG. 12 shows a handpiece 38 according to an embodiment of the present invention wherein a cooling member 185 for cooling of the tissue to be treated is provided. The cooling member has an adapter for adapting the cooling member 185 to the handpiece. Further, a flexible hose 187 with thermal isolation is provided to connect the cooling member with a cooling system 188. A removable cooling attachment 203 is provided to the flexible hose 187 to easily connect and disconnect the cooling member 185 to the cooling system 188 via the flexible hose 187.

The cooling system 188 is connected to microprocessor 190, where from it is controlled. A user interface 191 is provided. The fluid coming from the cooling member via line 192 is directed to a cooling fluid reservoir 193 wherein also air is removed from the fluid. The fluid is via a particle filter 194 led to a fluid pump 195 controlled by microprocessor 190. The fluid pump 195 leads the fluid to a heat exchanger 196. TE coolers 197 are positioned next to the heat exchanger 196 and controlled by the microprocessor 190. A heat sink 198 and fans 199 for cooling the heat sink is provided. The fans 199 also being controlled by the microprocessor 190. Power drives 200, 201, 202 are provided for respectively, the fans 199, the TE-coolers 197 and the fluid pump 195. The fluid from the heat exchanger is led to an outlet 204 via the flexible hose 187, to be used in the cooling member 185.

Figure 13:
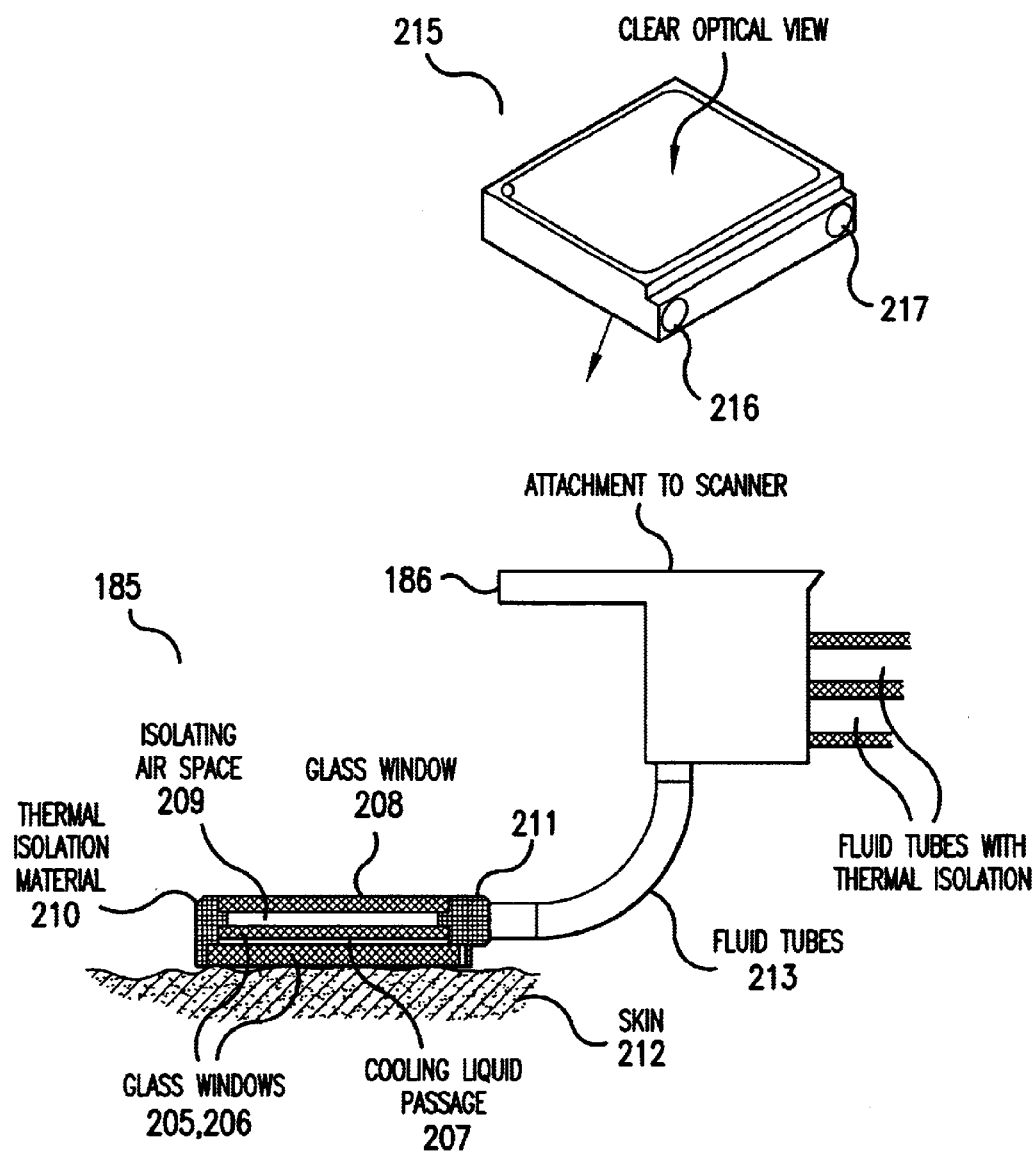
FIG. 13 shows the cooling member in more detail.

FIG. 13 shows the cooling member 185 in more detail. The cooling member 185 is positioned at the tissue to be treated 212. The upper and the lower glass window 205, 206, respectively, are positioned in a frame 210, 211 and connected so as to form a volume 207, wherein the fluid may flow. The volume 207 is optimised to get a uniform liquid flow. Above the upper and the lower glass windows 205, 206, a third glass window 208 is positioned in the frame 210, 211 so as to create an isolating air space 209 between the glass windows 205, 206 and the glass window 208. Hereby, the third glass window 208 prevents condensation. The frame 210, 211 comprises thermal isolation material for isolation purposes. A fluid tube 213 is connected to the adapter for attachment to a scanner, where from fluid tubes 214 leads to the cooling system. Also in FIG. 13 a top view 215 of the cooling member 185 is shown. An inlet 216 for inletting cooling fluid and an outlet 217 for outletting cooling fluid from the volume is provided at one side of the cooling member and the cooling member 185 is via coatings on the windows 205, 206 and 208 transparent to the light beams used during treatment.

What is claimed is:

1. An apparatus for tissue treatment comprising
    a light source for emission of a treating light beam towards tissue to be treated,
    a handpiece with an output for emission of the treating light beam,
    a detector means for detection of at least one tissue parameter along a predetermined path during a first scan,
    storage means for storage of coherent data sets of signal values provided by the detector means at positions along the predetermined path and the respective corresponding positions,
    first deflection means for scanning the treating light beam across tissue to be treated,
    deflection control means for controlling the first deflection means in such a way that the treating light beam is deflected along the predetermined path across the tissue to be treated during a second scan,
    light beam control means for controlling at least one parameter of the treating light beam during the second scan, and
    a display for displaying a map of the at least one tissue parameter, wherein the light beam control means is adapted to control at least one parameter of the treating light beam along the predetermined path in accordance with the stored data sets.

2. An apparatus according to claim 1, further comprising a camera for recording a tissue area and wherein a map of the recorded tissue area is displayed on the display.

3. An apparatus according to claim 1, further comprising a scanner for scanning the viewing field of the detector across a tissue area and wherein a map of features of the scanned tissue area is displayed on the display.

4. An apparatus according to claim 1, further comprising image processing means for processing the map for enhancement of selected tissue features.

5. An apparatus according to claim 1, further comprising user interface means for user selection of specific mapped tissue areas for treatment.

6. An apparatus according to claim 1, wherein the treating light beam is controlled without interruption of the treating light beam.

7. An apparatus according to claim 1, wherein the at least one detected tissue parameter is selected from the group consisting of texture, elasticity, size, and shape.

8. An apparatus according to claim 1, wherein the display is positioned on the handpiece.

9. An apparatus according to claim 1, further comprising an optical fibre for transmission of the treating light beam from the light source to the handpiece.

10. An apparatus according to claim 10, further comprising a processor that is adapted to process detected tissue parameter data for recognition of tissue features.

11. An apparatus according to claim 10, wherein the processor is adapted to provide the map to the display.

12. An apparatus according to claim 11, wherein the processor is adapted to enhance tissue features on the display.

13. An apparatus according to claim 1, wherein the detector means comprises light detectors for detection of intensity of light emitted from tissue.

14. An apparatus according to claim 1, wherein the detector means comprises infrared detectors for detection of temperature of tissue.

15. An apparatus according to claim 13 or 14, wherein several maps are displayed on the display simultaneously.

16. An apparatus for tissue treatment and having a light source for emission of a treating light beam towards tissue to be treated, detector means for detection of tissue temperature and a display for displaying a map of tissue temperature.

17. An apparatus according to claim 16, wherein the detector means for detection of tissue temperature comprises infrared detectors.

18. An apparatus according to claim 16, wherein the display is displaying the actual temperature of tissue to be treated before, during and/or after treatment.

19. An apparatus according to claim 16, wherein the display is displaying the mean temperature of tissue to be treated before, during and/or after treatment.

20. An apparatus according to claim 16, further comprising a scanner for scanning the viewing field of the detector across a tissue area and wherein a map of the temperature of the scanned tissue area is displayed on the display.

21. An apparatus according to claim 16, further comprising image processing means for processing the map.

22. An apparatus according to claim 16, further comprising user interface means for user selection of specific mapped tissue areas for treatment.

23. An apparatus according to claim 16, further comprising light beam control means for controlling at least one parameter of the light beam in response to the detected tissue temperature.

24. An apparatus according to claim 16, wherein the light beam is controlled without interruption of the treating light beam.

25. An apparatus according to claim 16, comprising a handpiece with an output for emission of the treating light beam.

26. An apparatus according to claim 16, wherein the display is positioned on the handpiece.

27. An apparatus according to claim 16, further comprising an optical fibre for transmission of the treating light beam from the light source to the handpiece.

28. An apparatus according to claim 16, further comprising first deflection means for scanning the treating light beam across tissue to be treated.

29. An apparatus according to claim 28, further comprising deflection control means for controlling the first deflection means in such a way that the treating light beam is deflected along a predetermined path across the tissue to be treated.

30. An apparatus according to claim 29, further comprising storage means for storage of coherent data sets of signal values provided by the detector means at positions along the predetermined path and the respective corresponding positions.

31. An apparatus according to claim 30, wherein the light beam control means is adapted to control at least one parameter of the light beam along the predetermined path in accordance with the stored data sets.

32. An apparatus according to claim 16, further comprising a processor that is adapted to process detected tissue temperature data.

33. An apparatus according to claim 32, wherein the processor is adapted to provide the map to the display.

34. An apparatus according to claim 16, wherein the detector means further comprises light detectors for detection of intensity of light emitted from tissue.

35. An apparatus according to claim 16, further comprising a camera for recording a issue area and wherein a map of the recorded tissue area is displayed on the display.

36. An apparatus according to claim 34 or 35, wherein several maps are displayed on the display simultaneously.

37. A method for tissue treatment comprising the steps of
emitting an illuminating light beam from a handpiece towards tissue to be treated,
detecting at least one tissue parameter by detection means along a predetermined path,
storing coherent data sets of signal values provided by the detector means at positions along the predetermined path and the respective corresponding positions,
displaying a map of the at least one tissue parameter,
emitting a treating light beam from a handpiece towards tissue to be treated
controlling first deflection means in such a way that the treating light beam is deflected along the predetermined path across the tissue to be treated, and
controlling at least one parameter of the light beam along the predetermined path in accordance with the stored data sets.

38. A method according to claim 37, further comprising the steps of recording a tissue area with a camera and displaying a map of the recorded tissue area.

39. A method according to claim 37, further comprising the steps of scanning the viewing field of the detector across a tissue area and displaying a map of features of the scanned tissue area.

40. A method according to claim 37, further comprising the step of processing the map for enhancement of selected tissue features.

41. A method according to claim 37, further comprising the step of user selection of specific mapped tissue areas for treatment.

42. A method according to claim 37, further comprising the step of controlling at least one parameter of the treating light beam in response to the detected tissue parameter.

43. A method according to claim 37, further comprising the step of processing detected tissue parameter data for recognition of tissue features.

44. A method according to claim 37, further comprising the step of enhancing tissue features on the display.

45. A method for tissue treatment comprising the steps of emission of a treating light beam towards tissue to be treated, detection of a tissue temperature and displaying a map of the tissue temperature.

46. A method according to claim 45, further comprising the steps of scanning the viewing field of the detector across a tissue area and displaying a map of the temperature of the scanned tissue area.

47. A method according to claim 45, further comprising the step of processing the map.

48. A method according to claim 45, further comprising the step of user selection of specific mapped tissue areas for treatment.

49. A method according to claim 45, further comprising the step of controlling at least one parameter of the treating light beam in response to the detected tissue temperature.

50. A method according to claim 45, further comprising the step of scanning the treating light beam across tissue to be treated.

51. A method according to claim 50, further comprising the step of controlling first deflection means in such a way that the treating light beam is deflected along a predetermined path across the tissue to be treated.

52. A method according to claim 51, further comprising the step of storage of coherent data sets of signal values provided by the detector means at positions along the predetermined path and the respective corresponding positions.

53. A method according to claim 52, further comprising the step of controlling at least one parameter of the light beam along the predetermined path in accordance with the stored data sets.

54. A method according to claim 45, further comprising the step of processing detected tissue temperature data.

55. A method according to claim 45, further comprising the steps of recording a tissue area with a camera and displaying a map of the recorded tissue area.

56. A method according to claim 55, further comprising the step of showing several maps simultaneously.

57. An apparatus according to claim 3, wherein the first deflection means comprises the scanner.

* * * * *